(12) United States Patent
Ohashi

(10) Patent No.: US 10,964,877 B2
(45) Date of Patent: Mar. 30, 2021

(54) PIEZOELECTRIC ELEMENT, PIEZOELECTRIC ACTUATOR, ULTRASONIC PROBE, ULTRASONIC APPARATUS, ELECTRONIC APPARATUS, LIQUID JET HEAD, AND LIQUID JET APPARATUS

(71) Applicant: Seiko Epson Corporation, Tokyo (JP)

(72) Inventor: Koji Ohashi, Matsumoto (JP)

(73) Assignee: Seiko Epson Corporation

( * ) Notice: Subject to any disclaimer, the term of this patent is extended or adjusted under 35 U.S.C. 154(b) by 496 days.

(21) Appl. No.: 15/935,492

(22) Filed: Mar. 26, 2018

(65) Prior Publication Data
US 2018/0277737 A1 Sep. 27, 2018

(30) Foreign Application Priority Data
Mar. 27, 2017 (JP) .............................. JP2017-061459

(51) Int. Cl.
*H01L 41/047* (2006.01)
*B06B 1/02* (2006.01)
(Continued)

(52) U.S. Cl.
CPC ............ *H01L 41/0475* (2013.01); *A61B 8/06* (2013.01); *A61B 8/085* (2013.01); *A61B 8/145* (2013.01); *A61B 8/4281* (2013.01); *A61B 8/4427* (2013.01); *A61B 8/4444* (2013.01); *A61B 8/4488* (2013.01); *A61B 8/4494* (2013.01); *B06B 1/0207* (2013.01);
(Continued)

(58) Field of Classification Search
CPC ............... H01L 41/0475; H01L 41/047; H01L 41/0973; H01L 41/1876; H01L 41/083; H01L 41/08; B41J 2/14274
See application file for complete search history.

(56) References Cited

U.S. PATENT DOCUMENTS 9,645,027 B2 * 5/2017 Hayashi .................. G01C 5/06
2001/0017503 A1 * 8/2001 Kitahara .............. B41J 2/14274
310/328
(Continued)

FOREIGN PATENT DOCUMENTS

JP 2013-046086 A 3/2013
JP 2014-195494 A 10/2014
JP 2015-066202 A 4/2015

OTHER PUBLICATIONS

Extended European Search Report for Application No. EP 18 16 3894 dated Jan. 24, 2019 (8 pages).

*Primary Examiner* — Bryan P Gordon
(74) *Attorney, Agent, or Firm* — Harness, Dickey & Pierce, P.L.C.

(57) ABSTRACT

A piezoelectric element includes a first electrode layer, a piezoelectric layer, and a second electrode layer. The first electrode layer, the piezoelectric layer, and the second electrode layer are stacked in sequence on one another. The first electrode layer has a first part overlapping the piezoelectric layer in a plan view, and a second part at least partially separated from the first part and not overlapping the piezoelectric layer in the plan view. The second electrode layer has a third part overlapping the piezoelectric layer in the plan view, and a fourth part separated from the third part. The fourth part is in contact with the first part and the second part.

16 Claims, 15 Drawing Sheets

(51) Int. Cl.

| | | |
|---|---|---|
| *H01L 41/04* | (2006.01) | |
| *H01L 41/09* | (2006.01) | |
| *H01L 41/332* | (2013.01) | |
| *H01L 41/317* | (2013.01) | |
| *B41J 2/14* | (2006.01) | |
| *A61B 8/14* | (2006.01) | |
| *A61B 8/00* | (2006.01) | |
| *B06B 1/06* | (2006.01) | |
| *B41J 2/16* | (2006.01) | |
| *A61B 8/08* | (2006.01) | |
| *A61B 8/06* | (2006.01) | |
| *G01N 29/24* | (2006.01) | |
| *H01L 41/187* | (2006.01) | |

(52) U.S. Cl.
CPC .......... *B06B 1/0622* (2013.01); *B06B 1/0666* (2013.01); *B41J 2/14233* (2013.01); *B41J 2/14274* (2013.01); *B41J 2/161* (2013.01); *B41J 2/1628* (2013.01); *H01L 41/042* (2013.01); *H01L 41/047* (2013.01); *H01L 41/0973* (2013.01); *H01L 41/317* (2013.01); *H01L 41/332* (2013.01); *B06B 2201/76* (2013.01); *G01N 29/2437* (2013.01); *H01L 41/0477* (2013.01); *H01L 41/1876* (2013.01)

(56) References Cited

U.S. PATENT DOCUMENTS

| | | |
|---|---|---|
| 2006/0279382 A1 | 12/2006 | Ohara et al. |
| 2013/0294202 A1* | 11/2013 | Hajati ................ G01S 15/8952 367/138 |
| 2014/0211592 A1 | 7/2014 | Miyazawa |
| 2014/0267504 A1 | 9/2014 | Ohashi et al. |
| 2014/0296716 A1 | 10/2014 | Kiyose et al. |
| 2015/0094590 A1 | 4/2015 | Kiyose et al. |
| 2015/0187347 A1* | 7/2015 | Kojima ................ H01L 41/332 310/322 |
| 2016/0027988 A1* | 1/2016 | Nagahata ............ B41J 2/1646 347/70 |

* cited by examiner

PIEZOELECTRIC ELEMENT, PIEZOELECTRIC ACTUATOR, ULTRASONIC PROBE, ULTRASONIC APPARATUS, ELECTRONIC APPARATUS, LIQUID JET HEAD, AND LIQUID JET APPARATUS

BACKGROUND

1. Technical Field

The present invention relates to a piezoelectric element, a piezoelectric actuator, an ultrasonic probe, an ultrasonic apparatus, an electronic apparatus, a liquid jet head, and a liquid jet apparatus.

2. Related Art

A known piezoelectric element for vibrating a driver such as a vibrating film is described in JP-A-2015-66202.

In JP-A-2015-66202, there is disclosed an ultrasonic device provided with a piezoelectric element. This ultrasonic device has a base body having a plurality of apertures respectively provided with vibrating films, and on each of the vibrating films, there is disposed a piezoelectric element formed of a lower electrode, a piezoelectric layer, and an upper electrode stacked on one another. Further, on the surface of the base body, there is disposed a plurality of first conductive films in a column direction, and a plurality of second conductive films in a row direction. The first conductive films each form the lower electrodes on the vibrating films, and the second conductive films each form the upper electrodes on the vibrating films.

Incidentally, in such a piezoelectric element as in JP-A-2015-66202 described above, the formation material of the piezoelectric layer is formed on the first conductive layer on the base body, and then the formation material is etched by ion milling or the like to thereby pattern the piezoelectric layer. When etching the piezoelectric layer, a part of the first conductive layer is thinned due to over etching. In particular, in an edge part of the piezoelectric layer, the etch rate becomes high, and breaking occurs in the first conductive layer in some cases. If breaking occurs in the first conductive layer as described above, the piezoelectric element deteriorates in function or becomes unable to drive, and there arises a problem that the reliability of the piezoelectric element degrades.

SUMMARY

An advantage of some aspects of the invention is to provide a piezoelectric element, a piezoelectric actuator, an ultrasonic probe, an ultrasonic apparatus, an electronic apparatus, a liquid jet head, and a liquid jet apparatus each high in reliability.

A piezoelectric element according to an application example of the invention includes a first electrode layer, a piezoelectric layer, and a second electrode layer, the first electrode layer, the piezoelectric layer, and the second electrode layer are stacked in sequence on one another, the first electrode layer has a first part overlapping the piezoelectric layer in a plan view viewed from a stacking direction of the first electrode layer, the piezoelectric layer, and the second electrode layer, and a second part at least partially separated from the first part and not overlapping the piezoelectric layer in the plan view, the second electrode layer has a third part overlapping the piezoelectric layer in the plan view, and a fourth part separated from the third part, and the fourth part has contact with the first part and the second part.

In this application example, the first electrode layer is provided with the first part overlapping the piezoelectric layer in the plan view and the second part not overlapping the piezoelectric layer and partially separated from the first part. Further, the second electrode layer is provided with the third part overlapping the piezoelectric layer to sandwich the piezoelectric layer together with the first part, and the fourth part separated from the third part. Further, the fourth part has contact with the first part and the second part of the first electrode layer. Therefore, it results that the first part and the second part of the first electrode layer are electrically connected to each other by the fourth part of the second electrode layer, and thus, the problem that breaking occurs between the first part and the second part can be prevented. Therefore, it is possible to appropriately input the signal for driving the piezoelectric element from the second part to the first part of the first electrode layer, and thus, it is possible to provide the piezoelectric element high in reliability.

Further, since the fourth part of the second electrode layer is disposed separately from the third part, there is no chance for the first electrode layer and the second electrode layer to be electrically connected to each other via the fourth part, and it is possible to appropriately apply the drive voltage to the piezoelectric layer using the first part of the first electrode layer and the third part of the second electrode layer to drive the piezoelectric element.

In the piezoelectric element according to the application example, it is preferable that the fourth part fills in the separated part between the first part and the second part.

In the application example with this configuration, the fourth part is disposed so as to fill in the separated part between the first part and the second part. Therefore, breaking between the first part and the second part can more surely be prevented to enhance the reliability of the piezoelectric element.

A piezoelectric element according to an application example of the invention includes a first electrode layer, a piezoelectric layer, a second electrode layer, a first conductive layer, and a second conductive layer, the first electrode layer, the piezoelectric layer, and the second electrode layer are stacked in sequence on one another, the first electrode layer and the second electrode layer overlap the piezoelectric layer in a plan view viewed from a stacking direction of the first electrode layer, the piezoelectric layer, and the second electrode layer, the first conductive layer is partially separated from the first electrode layer, and does not overlap the piezoelectric layer in the plan view, the second conductive layer is separated from the second electrode layer, and the second conductive layer has contact with the first electrode layer and the first conductive layer.

In this application example, the signal is input from the first conductive layer to the first electrode layer to thereby drive the piezoelectric layer. As such, since the first electrode layer and the first conductive layer have contact with the second conductive layer, even in the case in which there is a void between the first electrode layer and the first conductive layer, it is possible to electrically connect the first electrode layer and the first conductive layer to each other via the second conductive layer. In other words, in this application example, breaking between the first electrode layer and the first conductive layer can be prevented, and thus, it is possible to provide a piezoelectric element high in reliability.

In the piezoelectric element according to the application example, it is preferable that the second conductive layer is larger in thickness dimension (thicker) than the second electrode layer.

In the application example with this configuration, since the second conductive layer is larger in thickness dimension than the second electrode layer, it is possible to reduce the electrical resistance between the first electrode layer and the conductive layer, and thus, it becomes possible to apply a signal with a desired voltage value to the first electrode layer. Further, since the second electrode layer is smaller in thickness dimension (thinner) then the second conductive layer, it is possible to increase the displacement of the piezoelectric layer when applying the voltage between the first electrode layer and the second electrode layer.

In the piezoelectric element according to the application example, it is preferable that the second conductive layer fills in a separated part between the first electrode layer and the first conductive layer.

In the application example with this configuration, the second conductive layer is disposed so as to fill in the separated part between the first electrode layer and the first conductive layer. Therefore, breaking between the first electrode layer and the second conductive layer can more surely be prevented to enhance the reliability of the piezoelectric element.

A piezoelectric actuator according to an application example of the invention includes the piezoelectric element described above, and a driver driven by the piezoelectric element.

In this application example, the driver is driven by a piezoelectric element such as described above. Here, the piezoelectric element can appropriately input the signal to the first electrode layer similarly to the application examples described above, and thus, the reliability of the piezoelectric element can be enhanced. Therefore, the reliability in the piezoelectric actuator can also be enhanced.

An ultrasonic probe according to an application example of the invention includes the piezoelectric actuator described above, and a housing configured to house the piezoelectric actuator, and the piezoelectric element drives the driver to one of transmit and receive an ultrasonic wave.

The ultrasonic probe according to this application example houses the piezoelectric actuator in the housing, and vibrates the driver (vibrating section) with the piezoelectric element, and thus, it becomes possible to perform the transmission and reception of the ultrasonic wave. Here, the piezoelectric actuator is provided with the piezoelectric element capable of appropriately inputting the signal to the first electrode layer similarly to the application examples described above, and thus, the reliability of the piezoelectric actuator can be enhanced. Therefore, the reliability in the ultrasonic probe having such a piezoelectric actuator can also be enhanced.

An ultrasonic apparatus according to an application example of the invention includes the piezoelectric actuator described above, and a controller configured to control the piezoelectric actuator, and the piezoelectric element drives the driver to one of transmit and receive an ultrasonic wave.

The ultrasonic apparatus according to this application example can perform the transmission and the reception of the ultrasonic wave by controlling the piezoelectric actuator using the controller to drive the driver, and the controller can, for example, form an internal tomographic image of the test object or give a diagnosis on the internal structure of the test object based on the reception result of the ultrasonic wave. Here, the piezoelectric actuator is provided with the piezoelectric element capable of appropriately inputting the signal to the first electrode layer similarly to the application examples described above, and thus, the reliability of the piezoelectric actuator can be enhanced. Therefore, the reliability in the ultrasonic apparatus having such a piezoelectric actuator can also be enhanced.

An electronic apparatus according to an application example of the invention includes the piezoelectric element described above, and a controller configured to control the piezoelectric element.

The electronic apparatus according to this application example controls the piezoelectric actuator with the controller to drive the driver to thereby perform a variety of operations. As such an electronic apparatus, there can widely be used as, for example, a displacement detection sensor for detecting the displacement of the driver with the piezoelectric element besides a drive apparatus for driving the driver to displace the object. Here, the piezoelectric actuator is provided with the piezoelectric element capable of appropriately inputting the signal to the first electrode layer similarly to the application examples described above, and thus, the reliability of the piezoelectric actuator can be enhanced. Therefore, the reliability in the electronic apparatus having such a piezoelectric actuator can also be enhanced.

A liquid jet head according to an application example of the invention includes the piezoelectric actuator described above.

In the liquid jet head according to this application example, by driving the driver with the piezoelectric actuator, it is possible to jet the liquid reserved in, for example, a tank from a nozzle. Here, the piezoelectric actuator is provided with the piezoelectric element capable of appropriately inputting the signal to the first electrode layer similarly to the application examples described above, and thus, the reliability of the piezoelectric actuator can be enhanced. Therefore, the reliability in the liquid jet head having such a piezoelectric actuator can also be enhanced.

A liquid jet apparatus according to an application example of the invention is equipped with the liquid jet head described above.

In this application example, the liquid jet apparatus is equipped with the liquid jet head high in reliability as described above, and thus, the reliability in the liquid jet apparatus can also be enhanced.

BRIEF DESCRIPTION OF THE DRAWINGS

Embodiments of the invention will be described with reference to the accompanying drawings, wherein like numbers reference like elements.

DESCRIPTION OF EXEMPLARY EMBODIMENTS

First Embodiment

A first embodiment of the invention will hereinafter be described based on the drawings.

Figure 1:
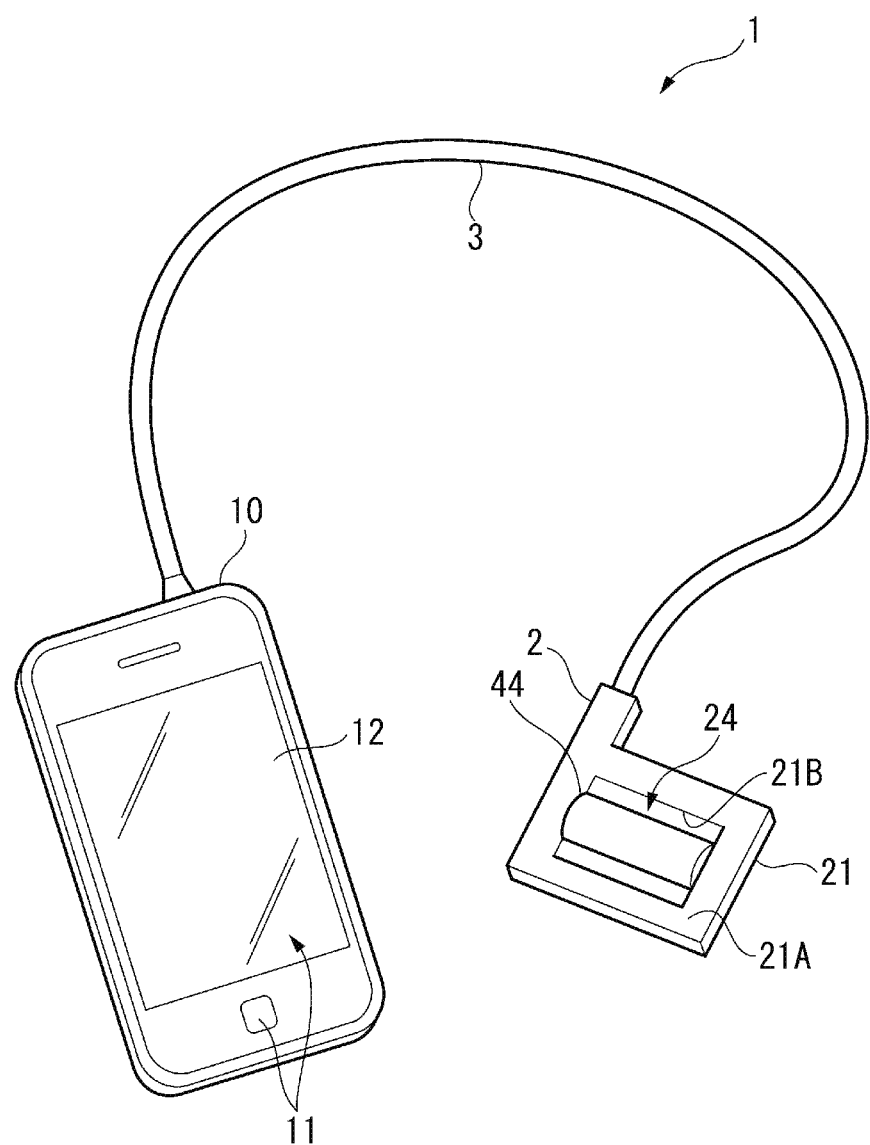
FIG. 1 is a perspective view showing a general configuration of an ultrasonic measurement apparatus according to a first embodiment of the invention.

FIG. 1 is a perspective view showing a schematic configuration of the ultrasonic measurement apparatus 1.

As shown in FIG. 1, the ultrasonic measurement apparatus 1 corresponds to the ultrasonic apparatus, and is provided with an ultrasonic probe 2, and a control device 10 electrically connected to the ultrasonic probe 2 via a cable 3.

The ultrasonic measurement apparatus 1 transmits an ultrasonic wave from the ultrasonic probe 2 to the inside of a living body (e.g., a human body) in the state in which the ultrasonic probe 2 has contact with a surface of the living body. Further, the ultrasonic measurement apparatus 1 receives the ultrasonic wave reflected by an organ in the living body using the ultrasonic probe 2 to, for example, obtain an internal tomographic image of the inside of the living body, or measure the state (e.g., blood flow) of the organ in the living body based on the received signal.

1. Configuration of Control Device

As shown in FIG. 1, for example, the control device 10 corresponds to a controller, and is provided with an operating interface 11 including buttons or a touch panel, and a display 12. Further, although not shown in the drawings, the control device 10 is provided with a storage section formed of a memory or the like, and an arithmetic section constituted by a central processing unit (CPU). The control device 10 makes the arithmetic section execute a variety of programs stored in the storage section to thereby control the ultrasonic measurement apparatus 1. For example, the control device 10 outputs a command for controlling the drive of the ultrasonic probe 2, forms an image of the internal structure of the living body and then makes the display 12 display the image, and measures the living body information such as the blood flow to make the display 12 display the living body information based on the received signal input from the ultrasonic probe 2. As such a control device 10, there can be used a terminal device such as a tablet terminal, a smartphone, or a personal computer, and a dedicated terminal device for operating the ultrasonic probe 2 can also be used.

2. Configuration of Ultrasonic Probe

Figure 2:
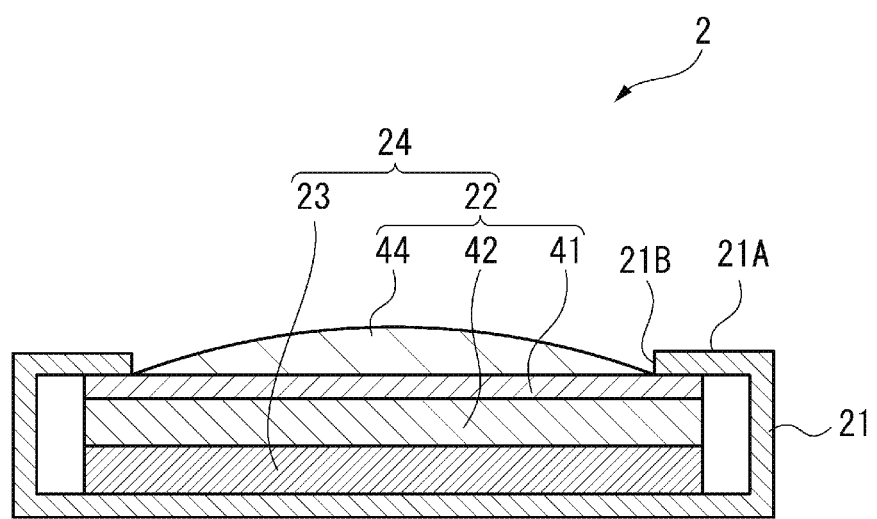
FIG. 2 is a cross-sectional view showing a schematic configuration of an ultrasonic probe according to the first embodiment.

FIG. 2 is a cross-sectional view showing a schematic configuration of the ultrasonic probe 2.

As shown in FIG. 2, the ultrasonic probe 2 is provided with a housing 21, an ultrasonic device 22 housed inside the housing 21, and a circuit board 23 provided with a driver circuit for controlling the ultrasonic device 22. It should be noted that the ultrasonic device 22 and the circuit board 23 constitute an ultrasonic sensor 24.

2-1. Configuration of Housing

As shown in FIG. 1, the housing 21 is formed to have a box-like shape having, for example, a rectangular planar shape, and on one surface (a sensor surface 21A) perpendicular to the thickness direction, there is disposed a sensor window 21B, and a part of the ultrasonic device 22 is exposed therefrom. Further, through a part (a side surface in the example shown in FIG. 1) of the housing 21, there is inserted the cable 3 connected to the circuit board 23 located inside the housing 21, and the ultrasonic probe 2 and the control device 10 are connected by the cable 3. It should be noted that the connection configuration between the ultrasonic probe 2 and the control device 10 is not limited thereto, but the ultrasonic probe 2 and the control device 10 are connected to each other with wireless communication, and further, a variety of constituents of the control device 10 can also be disposed inside the ultrasonic probe 2.

2-2. Configuration of Circuit Board

The circuit board 23 is electrically connected to signal terminals 51P (see FIG. 3) and common terminals 52P (see FIG. 3) of the ultrasonic device 22 described later to control the ultrasonic device 22 based on the control by the control device 10.

Specifically, the circuit board 23 is provided with a transmission circuit, a reception circuit. The transmission circuit outputs a drive signal for making the ultrasonic device 22 perform ultrasonic transmission. The reception circuit obtains a reception signal output from the ultrasonic device 22, which has received the ultrasonic wave, then performs an amplification process, an A-D conversion process, a phasing addition process of the reception signal, and then outputs the result to the control device 10.

2-3. Configuration of Ultrasonic Device

Figure 3:
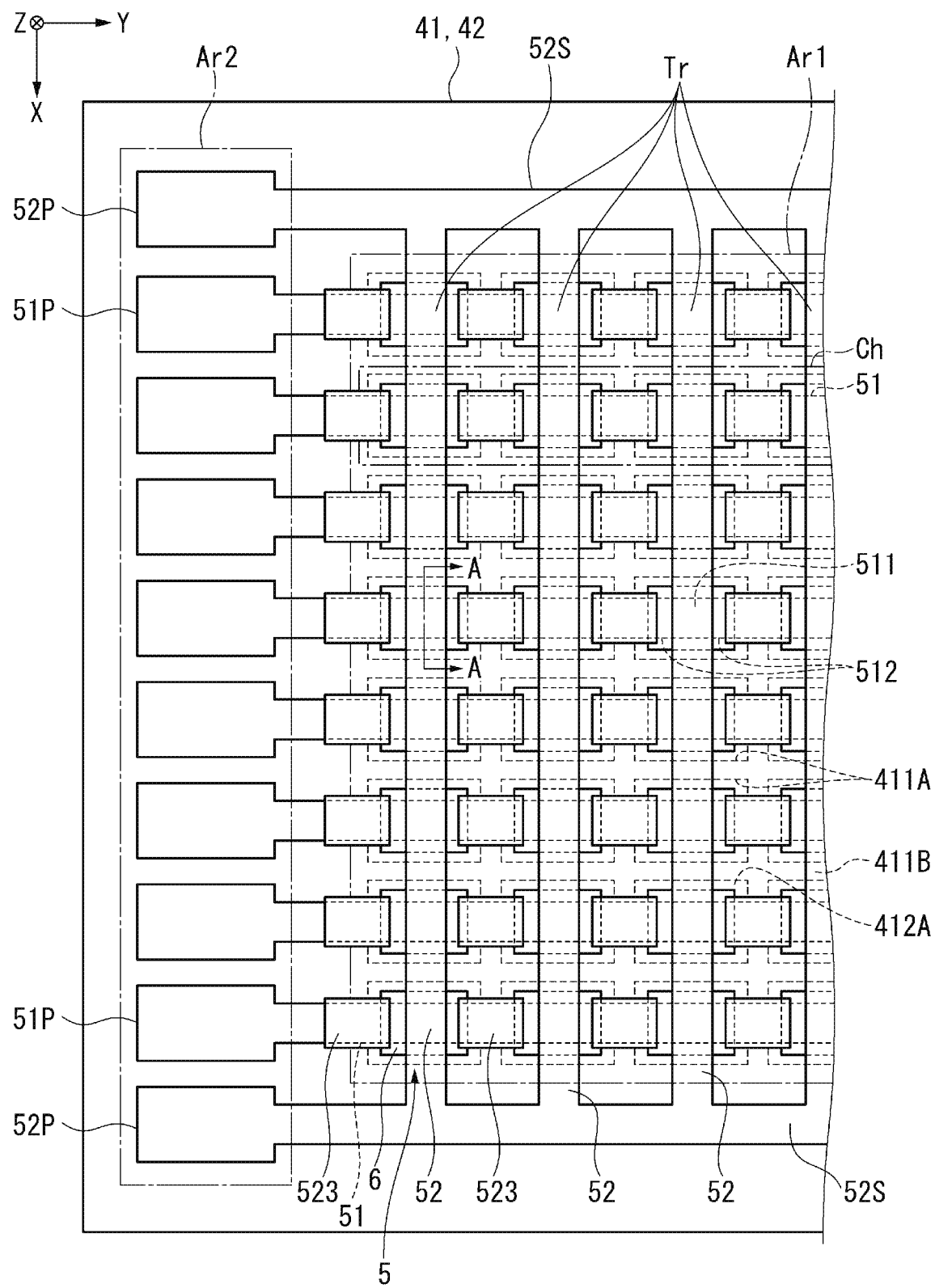
FIG. 3 is a plan view of apart of an element substrate constituting an ultrasonic device according to the first embodiment viewed from a sealing plate side.
Figure 4:
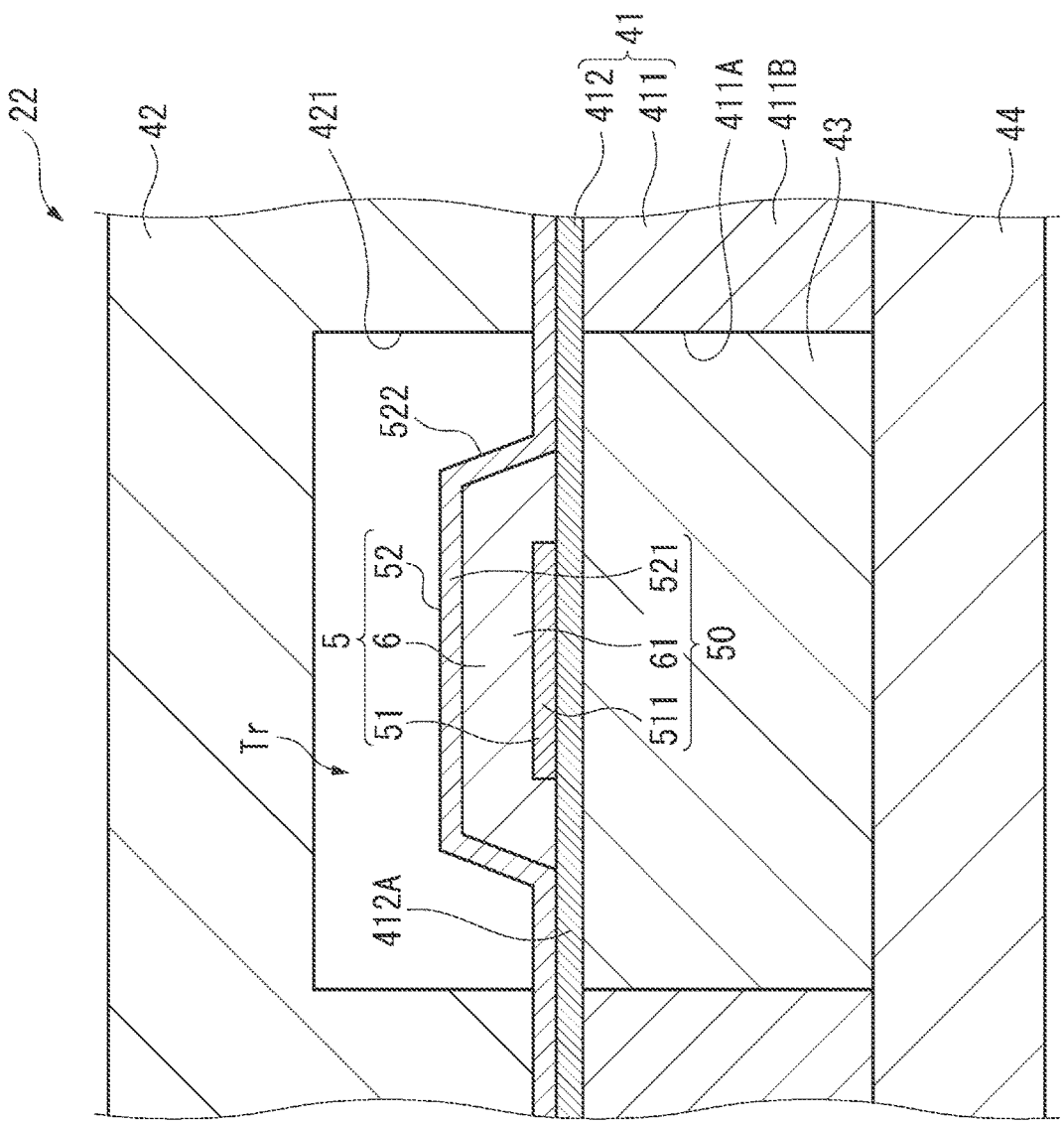
FIG. 4 is a cross-sectional view of the ultrasonic device cut along the line A-A shown in FIG. 3.

FIG. 3 is a plan view of a part of an element substrate 41 constituting the ultrasonic device 22 viewed from a sealing plate 42 side. FIG. 4 is a cross-sectional view of the ultrasonic device 22 cut along the line A-A shown in FIG. 3. It should be noted that in FIG. 3, the number of ultrasonic transducers Tr arranged is reduced for the sake of convenience of explanation, but in reality, there are arranged a larger number of ultrasonic transducers Tr.

As shown in FIG. 2 and FIG. 4, the ultrasonic device 22 is provided with the element substrate 41, the sealing plate 42 (a substrate), and an acoustic lens 44.

As shown in FIG. 3, the ultrasonic device 22 is provided with a plurality of ultrasonic transducers Tr arranged in a two-dimensional array along the X direction (a scanning direction) and the Y direction (a slicing direction) crossing each other (perpendicular to each other as an example in the present embodiment). In the present embodiment, 1-CH (channel) transmission/reception column Ch is constituted by a plurality of ultrasonic transducers Tr arranged in the Y direction. Further, a plurality of the 1-CH transmission/reception columns Ch arranged side by side along the X direction constitutes the ultrasonic device 22 having a one-dimensional array structure. Here, an area where the ultrasonic transducers Tr are arranged is defined as an array area Ar1.

2-3-1. Configuration of Element Substrate

As shown in FIG. 4, the element substrate 41 is provided with a substrate main body 411, and a vibrating film 412 disposed on the sealing plate 42 side (−Z side) of the substrate main body 411. Further, the vibrating film 412 is provided with a plurality of piezoelectric elements 5.

The substrate main body 411 is a substrate for supporting the vibrating film 412, and is formed of a semiconductor substrate made of, for example, Si. To the substrate main body 411, there are provided apertures 411A corresponding respectively to the ultrasonic transducers Tr.

In the present embodiment, each of the apertures 411A is a through hole penetrating the substrate main body 411 in the thickness direction thereof, and the vibrating film 412 is disposed so as to close one end side (the sealing plate 42 side) of the through hole.

The vibrating film 412 is formed of, for example, $SiO_2$ or a stacked body of $SiO_2$ and $ZrO_2$, and is disposed on the sealing plate 42 side of the substrate main body 411. The thickness dimension of the vibrating film 412 is small with respect to that of the substrate main body 411. The vibrating film 412 is supported by partition walls 411B constituting the aperture 411A, and closes the sealing plate 42 side of the aperture 411A. A part of the vibrating film 412 overlapping the aperture 411A in the plan view constitutes a flexible membrane 412A. In other words, the aperture 411A defines the outer edge of the flexible membrane 412A as a vibrating area of the vibrating film 412.

On the surface on the sealing plate 42 side of the flexible membrane 412A, there is disposed the piezoelectric element 5. It should be noted that although described later in detail, the piezoelectric element 5 is configured as a stacked body having a lower electrode 51, a piezoelectric film 6, and an upper electrode 52 stacked on one another in sequence. The flexible membrane 412A corresponds to a driver driven by the piezoelectric element 5, and the flexible membrane 412A and the piezoelectric element 5 constitute the ultrasonic transducer Tr as a piezoelectric actuator.

In such an ultrasonic transducer Tr, by applying a pulse-wave voltage having a predetermined frequency between the lower electrode 51 and the upper electrode 52, the flexible membrane 412A of the vibrating film 412 in an opening region of the aperture 411A is vibrated to transmit the ultrasonic wave from the aperture 411A side. Further, when the flexible membrane 412A is vibrated by the ultrasonic wave reflected by an object and entering the ultrasonic transducer Tr through the aperture 411A, a potential difference occurs between an upper part and a lower part of the piezoelectric film 6. Therefore, by detecting the electrical potential difference occurring between the lower electrode 51 and the upper electrode 52, the ultrasonic wave is detected, namely received.

Here, as shown in FIG. 3, the lower electrode 51 corresponds to a first electrode layer, and is formed linearly along the Y direction to constitute the 1-CH transmission/reception column Ch. Both end parts (the ±Y side end parts) of the lower electrode 51 extend to terminal areas Ar2 (the terminal area Ar2 on the −Y side is illustrated alone in FIG. 3) disposed on the ±Y side of the array area Ar1. Further, the tip of the lower electrode 51 in the terminal area Ar2 constitutes the signal terminal 51P to be electrically connected to the circuit board 23.

Further, the upper electrode 52 corresponds to a second electrode layer, and is formed to have a linear shape along the X direction. The ±X side end parts of the upper electrode 52 are respectively connected to common electrode lines 52S. The common electrode lines 52S each connect the upper electrodes 52 arranged along the Y direction to each other. Further, both end parts (±Y side end parts) of the common electrode line 52S are connected in the respective terminal areas Ar2 to the respective common terminals 52P to be electrically connected to the circuit board 23. The common terminals 52P are connected to, for example, a reference electrical potential circuit (not shown) of the circuit board 23, and are set to the reference electrical potential.

It should be noted that a detailed description of the piezoelectric element 5 will be described later.

2-3-2. Configuration of Sealing Plate

The sealing plate 42 shown in FIG. 2 and FIG. 4 is formed to have the same planar shape when viewed from the thickness direction as that of, for example, the element substrate 41, and is formed of a semiconductor substrate made of Si or the like, or an insulator substrate. It should be noted that the material and the thickness of the sealing plate 42 affect the frequency characteristics of the ultrasonic transducer Tr, and are therefore preferably set based on the central frequency of the ultrasonic wave transmitted/received by the ultrasonic transducer Tr.

The sealing plate 42 has a plurality of concave grooves 421 (see FIG. 4), which correspond to the apertures 411A, in an area opposed to the array area Ar1 of the element substrate 41. Thus, it results that a gap having a predetermined dimension is provided between the element substrate 41 and the area (inside the aperture 411A) where the flexible membrane 412A is formed out of the vibrating film 412, and thus, the vibration of the vibrating film 412 is prevented from being hindered. Further, the problem (cross talk) that the back wave from one ultrasonic transducer Tr enters another adjacent ultrasonic transducer Tr can be prevented from occurring.

Further, the sealing plate 42 is provided with a connecting section for connecting the terminals 51P, 52P to the circuit board 23 disposed at a position opposed to the terminal area Ar2 of the element substrate 41. As the connecting section, there is a configuration including, for example, an aperture provided to the element substrate 41, and a wiring member such as flexible printed circuits (FPC), cable lines, or wires for connecting the terminals 51P, 52P and the circuit board 23 to each other via the aperture.

2-3-3. Configuration of Acoustic Layer and Acoustic Lens

As shown in FIG. 4, the acoustic matching layer 43 is disposed on an opposite side to the sealing plate 42 of the element substrate 41, and fills the aperture 411A.

The acoustic lens 44 is disposed on the opposite side to the sealing plate 42 of the element substrate 41, namely the +Z side of the element substrate 41 and the acoustic layer 43. The acoustic lens 44 is applied to the living body surface, and converges the ultrasonic wave inside the living body, wherein the ultrasonic wave has been transmitted from the ultrasonic transducer Tr. Further, the acoustic lens 44 makes the ultrasonic wave having been reflected inside the living body propagate to the ultrasonic transducer Tr via the acoustic layer 43.

2-3-4. Configuration of Piezoelectric Element

Next, the configuration of the piezoelectric element 5 will be described in more detail.

Figure 5:
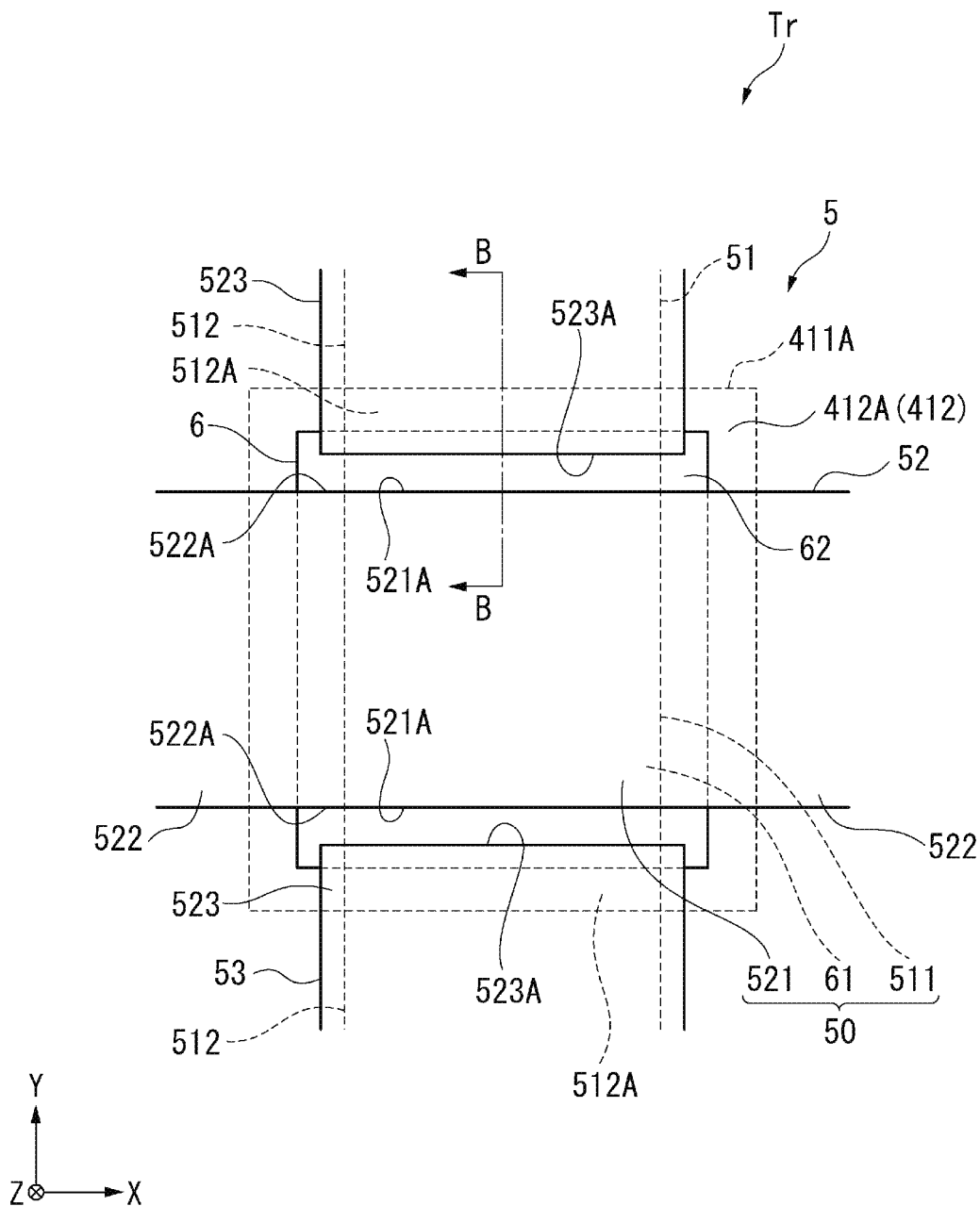
FIG. 5 is a plan view of an ultrasonic transducer provided to the element substrate of the first embodiment viewed from the sealing plate side.
Figure 6:
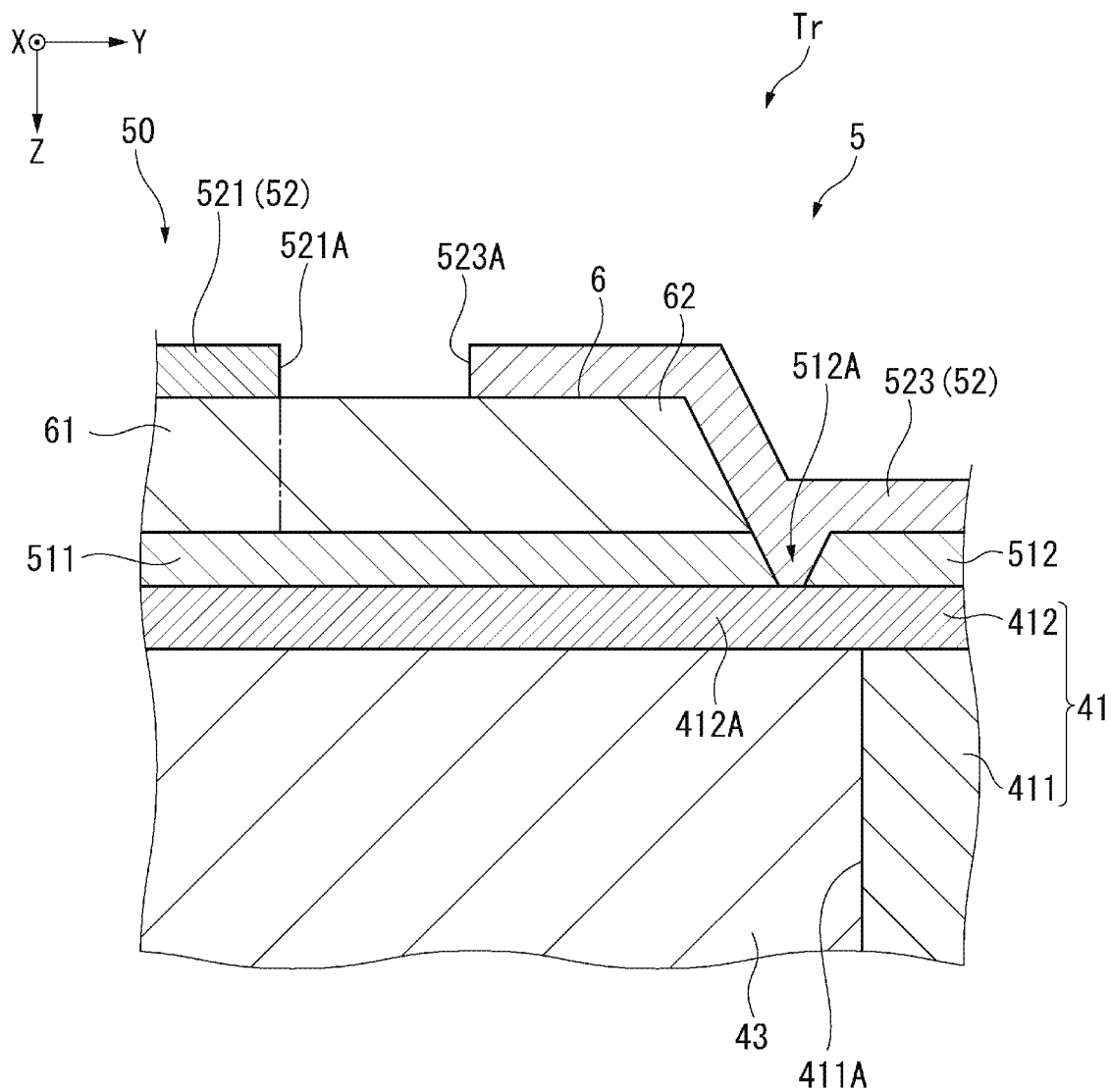
FIG. 6 is a cross-sectional view of a part of the ultrasonic transducer cut along the line B-B shown in FIG. 5.

FIG. 5 is a plan view of the ultrasonic transducer Tr provided to the element substrate 41 viewed from the sealing plate 42 side. FIG. 6 is a cross-sectional view of a part of the ultrasonic transducer Tr cut along the line B-B shown in FIG. 5.

As described above, the piezoelectric element 5 is provided with the lower electrode 51, the piezoelectric film 6, and the upper electrode 52, and among these constituents, a part (columnar stack) where the lower electrode 51, the piezoelectric film 6, and the upper electrode 52 overlap each other in the plan view viewed from the stacking direction constitutes an active section 50. The active section 50 is a part which deforms due to voltage application to the lower electrode 51 and the upper electrode 52, and is located on the flexible membrane 412A to constitute the ultrasonic transducer Tr.

The piezoelectric film 6 corresponds to the piezoelectric layer, and is formed using, for example, a transition metal oxide having a perovskite structure, specifically, lead zirconate titanate including Pb, Ti, and Zr.

The piezoelectric film 6 has, for example, a roughly rectangular outer shape, and is disposed at a position where the piezoelectric film 6 overlaps the flexible membrane 412A so as to cover a part of the lower electrode 51 in the plan view. The piezoelectric film 6 has a piezoelectric main body 61 and a piezoelectric outer periphery 62.

As shown in FIG. 5, the piezoelectric main body 61 is a part overlapping both of the lower electrode 51 and the upper electrode 52 (except a connection electrode part 523 described later), and constitutes the active section 50.

In the plan view, the piezoelectric outer periphery 62 is a part that is continuous with the outside of the piezoelectric main body 61 but does not overlap either or both of the lower electrode 51 and the upper electrode 52 (except the connection electrode part 523 described later).

The lower electrode 51 corresponds to the first electrode layer, and is formed of a metal material such as Pt, Ir, Ti, Zr, Au, Ni, NiCr, TiW, Al, or Cu. As shown in FIG. 5, the lower electrode 51 is provided with lower electrode main bodies 511 and lower electrode connection parts 512.

The lower electrode main body 511 corresponds to a first part, and overlaps the piezoelectric film 6 in the plan view. Apart of the lower electrode main body 511 overlapping the piezoelectric film 6 (a piezoelectric main body 61) and the upper electrode 52 (an upper electrode main body 521) constitutes the active section 50.

The lower electrode connection parts 512 each correspond to a second part, and are parts respectively extending along the Y direction from the ±Y sides of the lower electrode main body 511 and not overlapping the piezoelectric film 6. The lower electrode connection parts 512 each connect the adjacent lower electrode main bodies 511 of the plurality of ultrasonic transducers Tr to each other, wherein the plurality of ultrasonic transducers Tr is included in the transmission/reception column Ch.

The upper electrode 52 corresponds to the second electrode layer, and is formed of a metal material such as Pt, Ir, Ti, Zr, Au, Ni, NiCr, TiW, Al, or Cu. As shown in FIG. 5, the upper electrode 52 is provided with upper electrode main bodies 521, upper electrode connection parts 522, and connection electrode parts 523.

The upper electrode main body 521 corresponds to a third part, and overlaps the lower electrode main body 511 and the piezoelectric main body 61 in the plan view to constitute the active section 50.

The upper electrode connection part 522 continuously extends along the X direction from each of the ±X sides of the upper electrode main body 521 to connect the adjacent upper electrode main bodies 521 to each other in the X direction. In the present embodiment, end edges 521A on the ±Y sides of the upper electrode main body 521 and end edges 522A on the ±Y sides of the upper electrode connection part 522 continue along a straight line.

The connection electrode part 523 corresponds to a fourth part, and is disposed continuously from each of the ±Y sides of the piezoelectric outer periphery 62 of the piezoelectric film 6 to the lower electrode connection part 512. Further, as shown in FIG. 3, it is also possible for the connection electrode part 523 to be disposed continuously between the piezoelectric outer peripheries 62 of the ultrasonic transducers Tr adjacent to each other in the Y direction.

Here, an end edge 523A on the −Y side of the connection electrode part 523 disposed on the +Y side is displaced toward the +Y side as much as a predetermined dimension from the end edges 521A, 522A on the +Y side of the upper electrode main body 521 and the upper electrode connection part 522. Further, the end edge 523A on the +Y side of the connection electrode part 523 disposed on the −Y side is displaced toward the −Y side as much as a predetermined dimension from the end edges 521A, 522A on the −Y side of the upper electrode main body 521 and the upper electrode connection part 522. In other words, the connection electrode part 523 is disposed separately from the upper electrode main body 521 and the upper electrode connection part 522.

Figure 7:
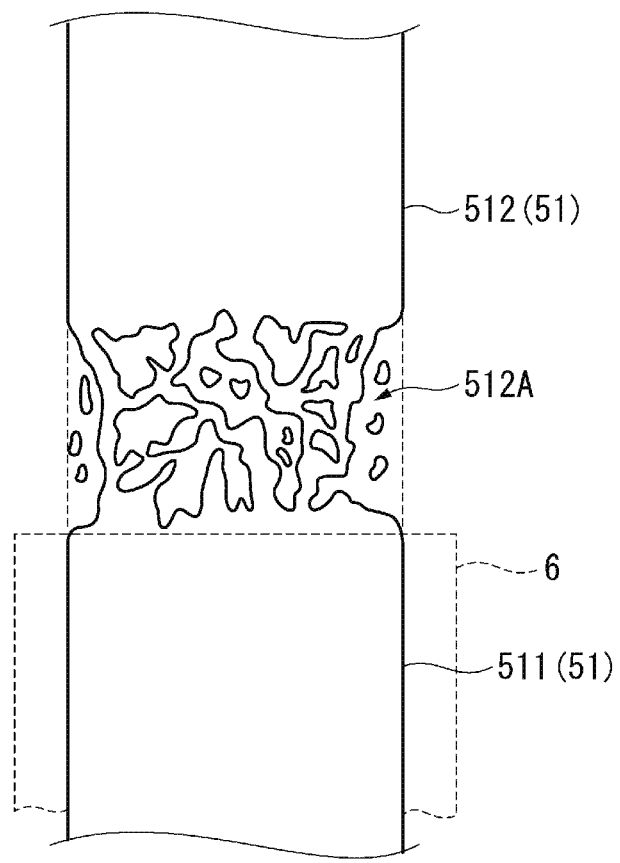
FIG. 7 is a diagram showing an example of a vicinity of a boundary between a lower electrode main body and a lower electrode connection part formed on the vibrating film of the first embodiment.
Figure 8:
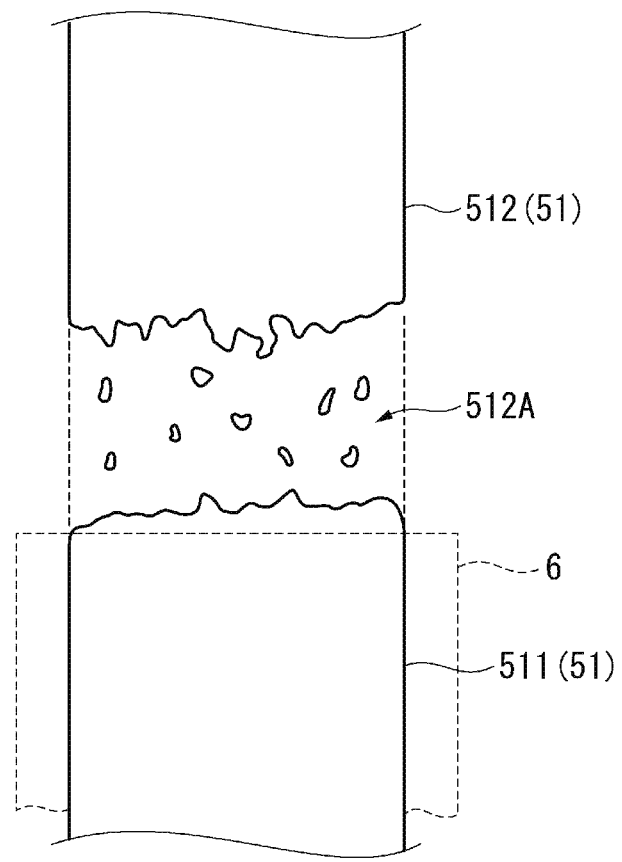
FIG. 8 is a diagram showing another example of the vicinity of the boundary between the lower electrode main body and the lower electrode connection part formed on the vibrating film of the first embodiment.

FIG. 7 and FIG. 8 are each a diagram showing an example of a vicinity of a boundary between the lower electrode main body 511 and a lower electrode connection part formed on the vibrating film 412.

Incidentally, in the present embodiment, between the lower electrode main body 511 and the lower electrode connection part 512, there is provided a shape including at least a part where the lower electrode main body 511 and the lower electrode connection part 512 are separated from each other as shown in FIG. 7 and FIG. 8.

That is, the piezoelectric element 5 according to the present embodiment is manufactured by forming the lower electrode 51, then depositing the piezoelectric layer 60 (see FIG. 10) for forming the piezoelectric film 6, and then patterning the piezoelectric layer 60 by dry etching (ion milling).

As such, if the piezoelectric layer 60 remains in positions other than the formation position of the ultrasonic transducer Tr, there is a possibility that the performance of the ultrasonic device 22 deteriorates. For example, if the piezoelectric layer 60 remains on the flexible membrane 412A at a position other than the ultrasonic transducer Tr, the stress balance of the flexible membrane 412A is lost to affect the frequency and the acoustic pressure of the ultrasonic waves which can be transmitted or received. Therefore, it is necessary to perform the etching process taking a sufficiently long time so that the piezoelectric layer 60 does not remain other positions than the position where the ultrasonic transducer Tr is formed. However, in the outer edge (an edge part) of the piezoelectric film 6, the etching rate increases to a higher rate compared to those in other positions, and thus, the connection part between the lower electrode connection part 512 and the lower electrode main body 511 is over-etched.

Therefore, as shown in FIG. 7, on the lower electrode main body 511 side of the lower electrode connection part 512, there is provided the shape having at least a part separated from the lower electrode main body 511 (there is formed a void 512A). Further, if the over-etching is advanced, there is provided a shape of separating the lower electrode main body 511 and the lower electrode connection part 512 from each other as shown in, for example, FIG. 8 in some cases. If a shape such as shown in 7 is provided, the electrical resistance of the lower electrode connection part 512 increases to fail to input an appropriate signal to the lower electrode main body 511, and further, if a shape such as shown in FIG. 8 is provided, breaking occurs between the lower electrode main body 511 and the lower electrode connection part 512.

It should be noted that breaking in the invention is not limited to the shape in which the lower electrode connection part 512 is separated from the lower electrode main body 511 as shown in FIG. 8, but includes a shape in which a part of the lower electrode connection part 512 is separated from the lower main body 511 as shown in FIG. 7.

In contrast, in the present embodiment, as shown in FIG. 6, the connection electrode part 523 of the upper electrode 52 is disposed in the void 512A to have contact with both of the lower electrode main body 511 and the lower electrode connection part 512. Specifically, the separated part between the lower electrode main body 511 and the lower electrode connection part 512 formed in the void 512A is filled with the connection electrode part 523.

Thus, in the present embodiment, the piezoelectric layer 60 for forming the piezoelectric film 6 does not remain in any areas other than the ultrasonic transducers Tr, and at the same time, an increase in electrical resistance and breaking in the void 512A between the lower electrode main body 511 and the lower electrode connection part 512 are prevented.

2-3-5. Method of Manufacturing Piezoelectric Element

Next, a method of manufacturing a piezoelectric element 5 such as described above will be described.

Figure 9:
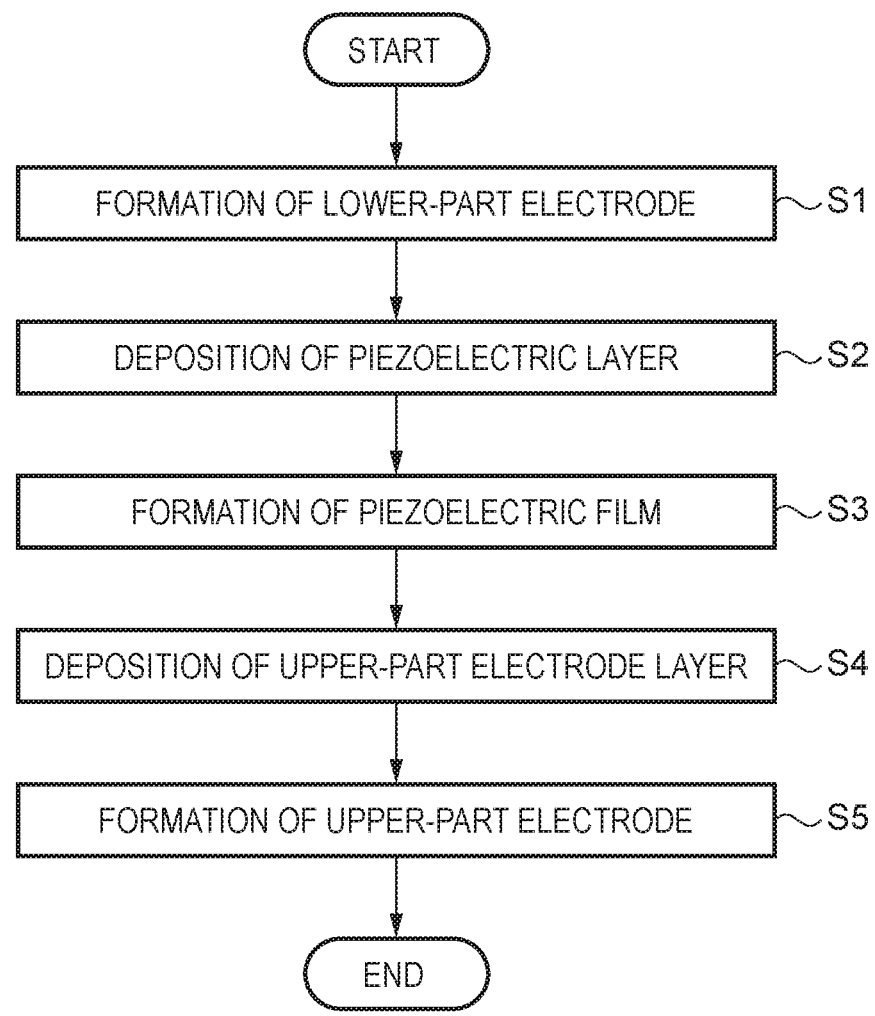
FIG. 9 is a flowchart showing a method of manufacturing a piezoelectric element according to the first embodiment.
Figure 10:
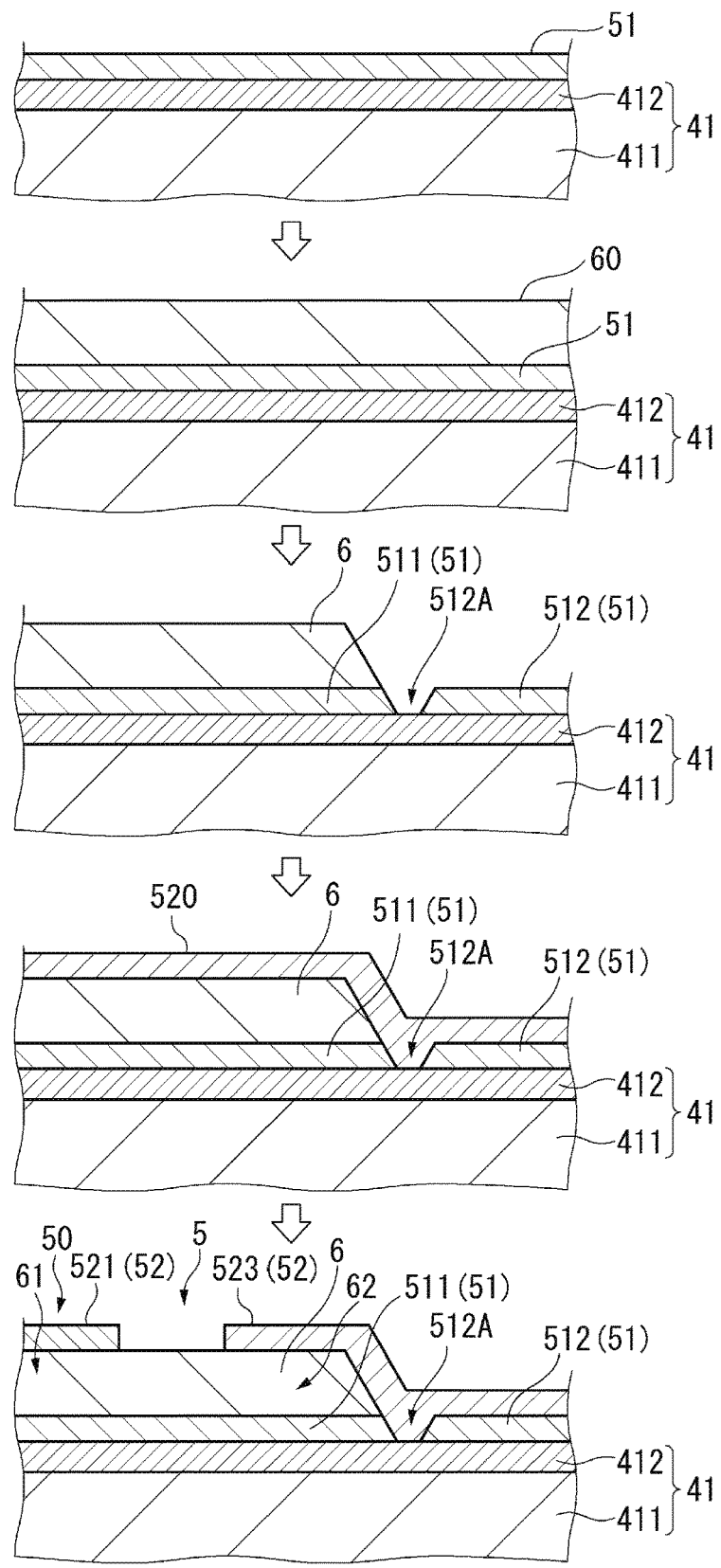
FIG. 10 is a diagram showing a manufacturing process of the piezoelectric element in the respective steps of FIG. 9.

FIG. 9 is a flowchart showing the method of manufacturing the piezoelectric element 5, and FIG. 10 is a diagram showing the manufacturing process of the piezoelectric element 5 in the respective steps of FIG. 9.

In order to manufacture the piezoelectric element 5, firstly, the lower electrode is formed (step S1). In the step S1, the lower electrode layer is deposited on the vibrating film 412 of the element substrate 41 provided with the vibrating film 412 using an electrode material constituting the lower electrode 51. Then, the lower electrode layer is patterned by etching to form the lower electrode 51 as shown in the first part of FIG. 10.

Then, the piezoelectric layer deposition is formed (step S2). In the step S2, as shown in the second part of FIG. 10, the piezoelectric layer 60 (PZT) covering the lower electrode 51 is formed on the vibrating film 412. In the formation of the piezoelectric layer 60, a coating process for applying a PZT solution on the vibrating film 412 and a calcination process for calcining the PZT solution thus applied are performed a plurality of times using, for example, a solution growth technique to form the piezoelectric layer 60 having a predetermined thickness.

Subsequently, the piezoelectric layer 60 is etched to be patterned (step S3) into a predetermined shape. In the step S3, the piezoelectric layer 60 is etched using dry etching (ion milling) to form the piezoelectric film 6 as shown in the third part of FIG. 10. As such, over-etching is advanced along the edge part of the piezoelectric film 6, and thus, a void 512A such as shown in FIG. 7 and FIG. 8 is formed on the lower electrode main body 511 side of the lower electrode connection part 512.

Then, there is deposited (step S4) an upper electrode layer 520 made of an electrode material for forming the upper electrode 52. In the step S4, the upper electrode layer 520 covering the lower electrode 51 and the piezoelectric film 6 is formed on the vibrating film 412 by, for example, sputtering. As such, as shown in the fourth part of FIG. 10, the upper electrode layer 520 is disposed in the void 512A formed in the step S3 (it can also be said that the void 512A is filled with the upper electrode layer 520).

Subsequently, the upper electrode layer 520 is etched to be patterned (step S5) into the upper electrode 52. Thus, as shown in the fifth part of FIG. 10, the connection electrode part 523 is formed at a position separated from the upper electrode main body 521 and the upper electrode connection part 522. Since the void 512A is filled with the connection electrode part 523, the lower electrode main body 511 and the lower electrode connection part 512 of the lower electrode 51 are connected to each other by the connection electrode part 523, and thus, the lower electrode main body 511 and the lower electrode connection part 512 are electrically connected to each other.

It should be noted that in the case of manufacturing the ultrasonic transducer Tr, an etching process is subsequently performed on the element substrate 41 from the surface on the opposite side to the vibrating film 412 to form the aperture 411A.

Functions and Advantages of Present Embodiment

In the present embodiment, the lower electrode 51 constituting the piezoelectric elements 5 has the lower electrode main bodies 511 each overlapping the piezoelectric film 6 in the plan view, and the lower electrode connection parts 512 not overlapping the piezoelectric film 6. The void 512A is formed on the lower electrode main body 511 side of the lower electrode connection part 512, and thus, the lower electrode connection part 512 is partially separated from the lower electrode main body 511. Meanwhile, the upper electrode 52 constituting the piezoelectric elements 5 is configured including the upper electrode main bodies 521 each overlapping the lower electrode main body 511 and the piezoelectric main body 61 to constitute the active section 50, and a connection electrode part 523 disposed separately from the upper electrode main bodies 521. The connection electrode part 523 is formed continuously from the piezoelectric outer periphery 62 of the piezoelectric film 6 to the lower electrode connection part 512, and has contact with the lower electrode main body 511 and the lower electrode connection part 512.

Therefore, it results that the connection electrode part 523 electrically connects the lower electrode main body 511 and the lower electrode connection part 512 to each other, and thus, it is possible to prevent the problem that breaking occurs between the lower electrode main body 511 and the lower electrode connection part 512. Therefore, it is possible to appropriately input a drive signal to the lower electrode main body 511 constituting the active section 50 from the lower electrode connection part 512, and thus, the reliability of the piezoelectric element 5 can be enhanced. Thus, it is also possible to enhance the equipment reliability in the ultrasonic transducer Tr, the ultrasonic probe 2, and the ultrasonic measurement apparatus 1 equipped with the piezoelectric element 5.

Further, since the connection electrode part 523 is disposed so as to fill in the void between the lower electrode main body 511 and the lower electrode connection part 512, breaking between the lower electrode main body 511 and the lower electrode connection part 512 can more surely be prevented, and thus, the reliability of the piezoelectric element 5 can be made higher.

In the present embodiment, the connection electrode part 523 can be made concurrently with the upper electrode main bodies 521 and the upper electrode connection part 522 by etching the upper electrode layer 520 in the step S5, and thus, the manufacturing efficiency can also be improved.

Second Embodiment

Hereinafter, a second embodiment of the invention will be described.

In the piezoelectric element 5 according to the first embodiment, the connection electrode part 523 as a part of the upper electrode 52 is formed in the step S5 at a position separated from the upper electrode main body 521, and the lower electrode main body 511 and the lower electrode connection part 512 are electrically connected to each other by the connection electrode part 523. In contrast, the second embodiment is different from the first embodiment described above in the point that the lower electrode main body 511 and the lower electrode connection part 512 are electrically connected by an electrode different from the upper electrode 52. It should be noted that in the following description, the constituents having already been described are denoted by the same reference symbols, and the description thereof will be omitted or simplified.

Figure 11:
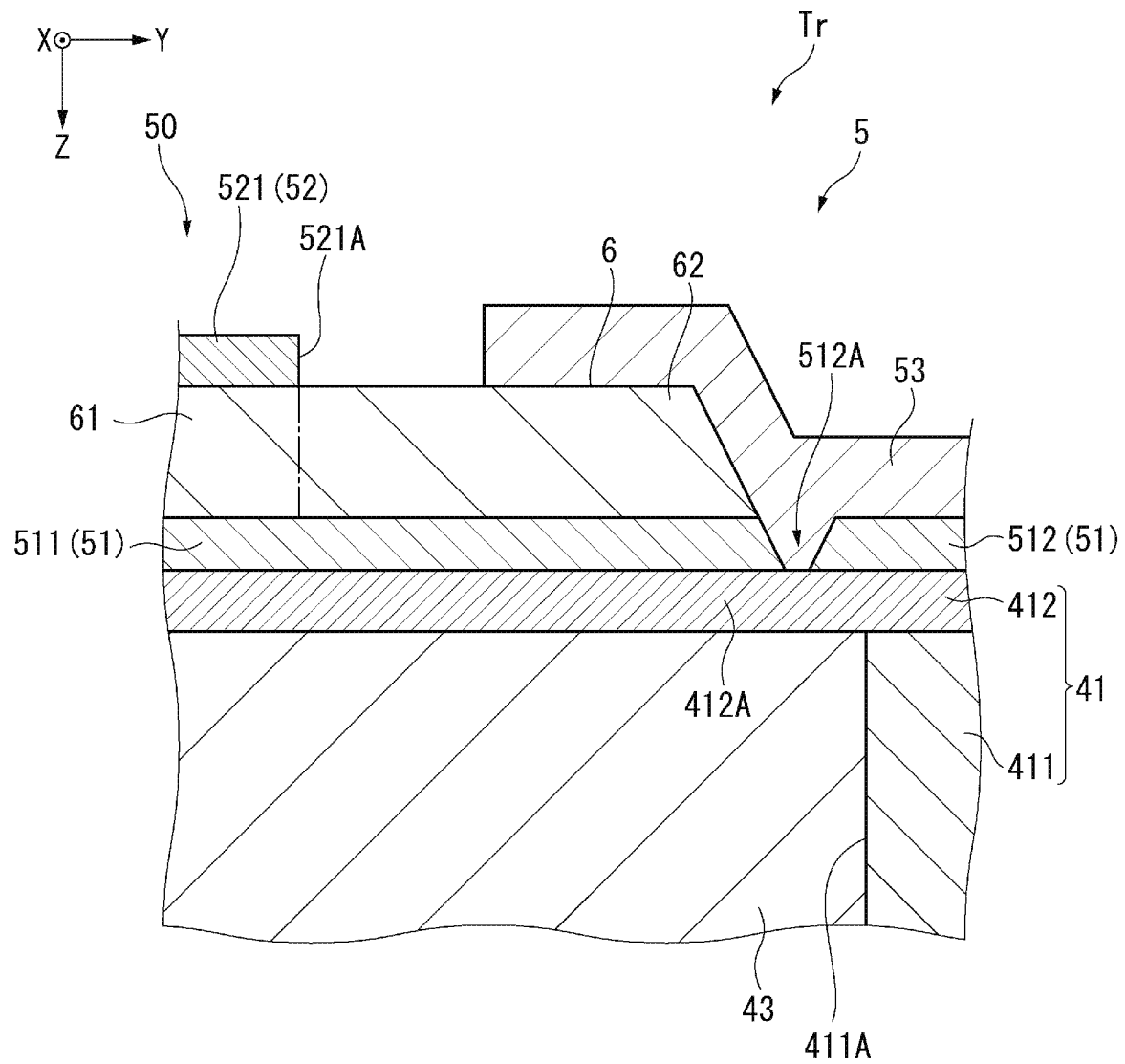
FIG. 11 is a cross-sectional view showing a part of an ultrasonic transducer according to a second embodiment of the invention.

FIG. 11 is a cross-sectional view showing an example of an ultrasonic transducer Tr according to the second embodiment.

Similarly to the first embodiment, the ultrasonic transducer Tr of the present embodiment is constituted by the flexible membrane 412A as the driver, and the piezoelectric element 5. The piezoelectric element 5 according to the present embodiment is formed by stacking the lower electrode 51, the piezoelectric film 6, and the upper electrode 52 on one another in sequence.

Here, the lower electrode 51 is formed of the lower electrode main bodies 511 and the lower electrode connection parts 512. Similarly to the first embodiment, the lower electrode connection part 512 is at least partially separated from the lower electrode main body 511, and the void 512A is formed on the lower electrode main body 511 side.

In the present embodiment, the lower electrode main body 511 corresponds to the first electrode layer, and the lower electrode connection part 512 corresponds to a first conductive layer. Similarly to the first embodiment, the lower electrode connection parts 512 are formed in the step S1 concurrently with the lower electrode main body 511. Further, when patterning the piezoelectric film 6 in the step S3, the end part on the lower electrode main body 511 side of the lower electrode connection part 512 is over-etched, and thus, the lower electrode connection part 512 is separated from the lower electrode main body 511 to form the void 512A.

The upper electrode 52 is provided with the upper electrode main body 521 and the upper electrode connection part 522. The upper electrode main body 521 corresponds to the second electrode layer in the present embodiment. The configuration of the upper electrode main body 521 and the upper electrode connection part 522 is the same as in the first embodiment described above.

Further, in the present embodiment, there is separately provided a connection electrode 53 as the second conductive layer independently of the upper electrode 52 described above. The connection electrode 53 is formed of, for example, the same electrode material as that of the upper electrode 52 continuously from the piezoelectric outer periphery 62 of the piezoelectric film 6 to the lower electrode connection part 512. Further, the connection electrode 53 is disposed in the void 512A of the lower electrode connection part 512 to have contact with the lower electrode main body 511 and the lower electrode connection part 512.

It should be noted that it is also possible for the connection electrode 53 to be disposed continuously between the piezoelectric outer peripheries 62 of the ultrasonic transducers Tr adjacent in the Y direction to each other so as to cover the lower electrode connection part 512 disposed between those ultrasonic transducers Tr similarly to the connection electrode part 523 in the first embodiment.

Further, in the present embodiment, the connection electrode 53 is formed to have larger thickness dimension compared to the upper electrode 52. In such a configuration, since the thickness dimension of the upper electrode 52 overlapping the active section 50 is reduced to increase the displacement of the active section 50, the transmission/reception sensitivity of the ultrasonic transducer Tr can be improved. Further, the thickness dimension of the connection electrode 53 is increased, to thereby make it possible to reduce the electrical resistance of the lower electrode connection part 512, and thus the voltage drop of the drive signal input to the lower electrode main body 511 can be suppressed.

Figure 12:
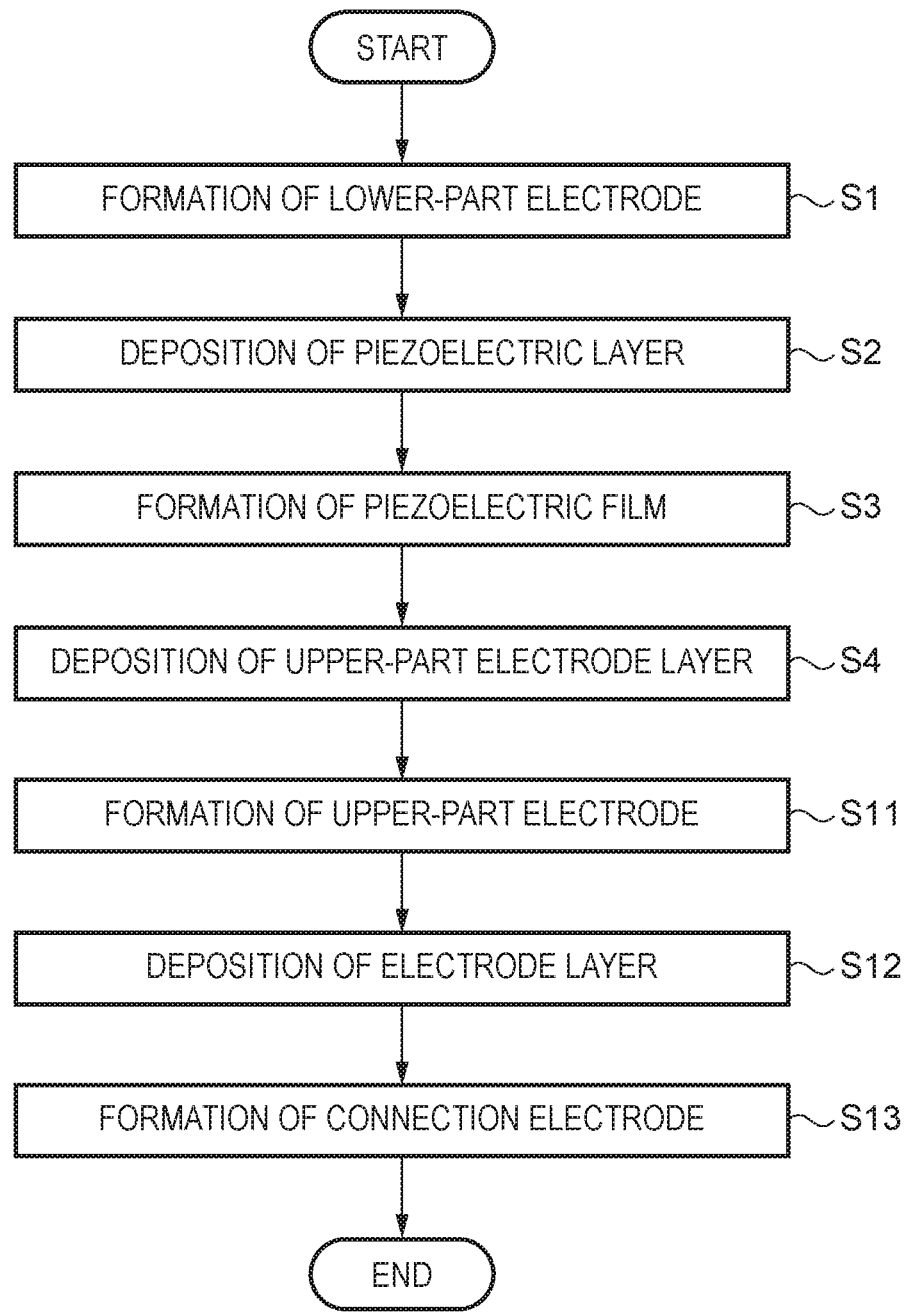
FIG. 12 is a flowchart showing a method of manufacturing a piezoelectric element according to the second embodiment.

FIG. 12 is a flowchart showing a method of manufacturing the piezoelectric element 5 according to the second embodiment.

The piezoelectric element 5 according to the second embodiment can be manufactured by roughly the same manufacturing method as in the first embodiment. Specifically, in the present embodiment, as shown in FIG. 12, firstly, the lower electrode 51 including the lower electrode main body 511 and the lower electrode connection part 512 is formed on the vibrating film 412 in the step S1.

Then, in the step S2, the piezoelectric layer 60 covering the lower electrode 51 is deposited on the vibrating film 412. Then, in the step S3, the piezoelectric layer 60 is etched to form the piezoelectric film 6 as shown in the third part of FIG. 10. As such, similarly to the first embodiment described above, over-etching is advanced along the edge part of the piezoelectric film 6, and thus, a void 512A such as shown in FIG. 7 and FIG. 8 is formed on the lower electrode main body 511 side of the lower electrode connection part 512.

Subsequently, the step S4 is performed to deposit the upper electrode layer 520 for forming the upper electrode 52. As such, the upper electrode layer 520 is deposited in accordance with the film thickness dimension of the upper electrode 52.

Figure 13:
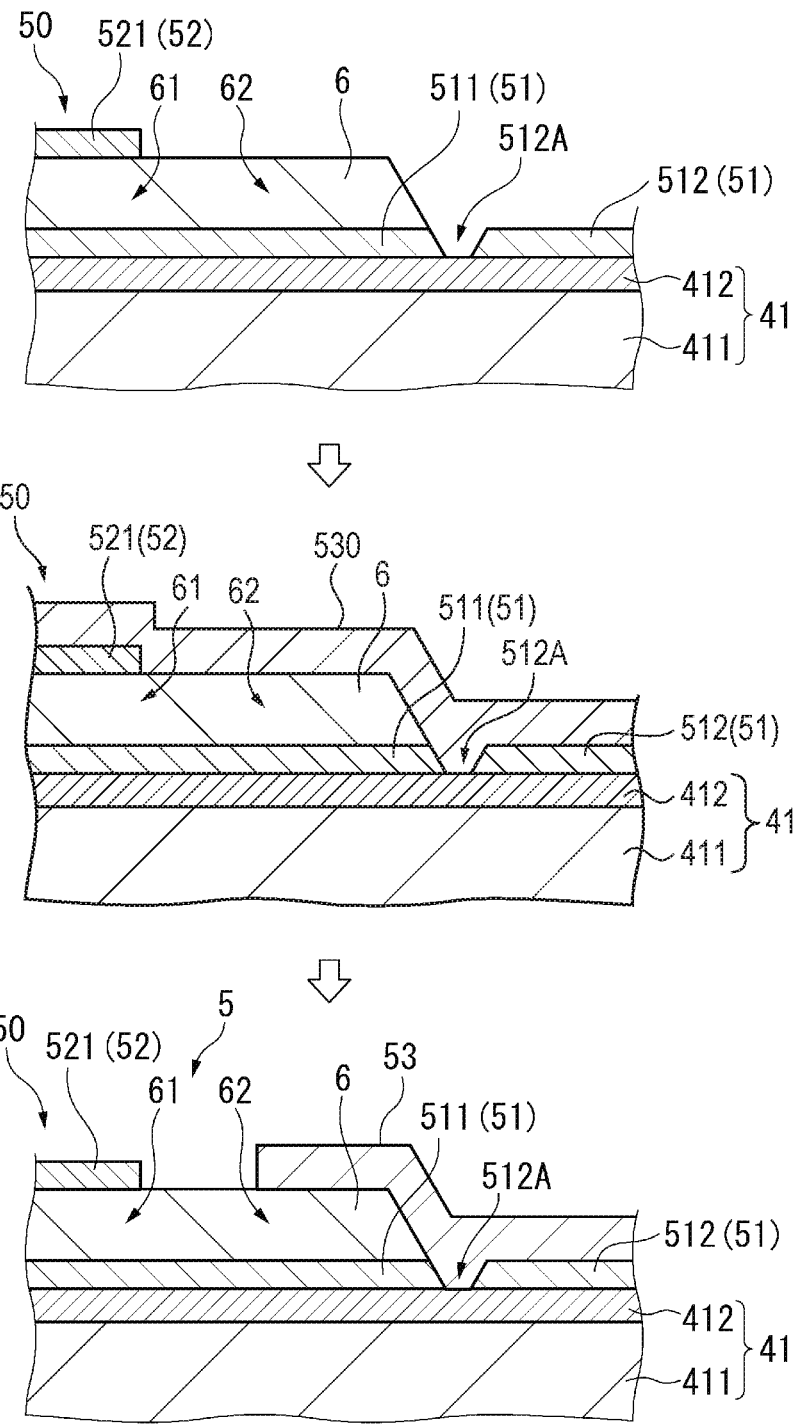
FIG. 13 is a diagram showing a manufacturing process of the piezoelectric element on and after the step S11 of FIG. 12.

FIG. 13 is a diagram showing the manufacturing process of the piezoelectric element 5 on and after the step S11 of FIG. 12.

Subsequently, patterning using etching is performed on the upper electrode layer 520 to form (step S11) the upper electrode 52 having the upper electrode main body 521 and the upper electrode connection part 522 as shown in the first part of FIG. 13. In the step S11, the lower electrode connection part 512 is at least partially separated from the lower electrode main body 511 in the void 512A.

Further, in the present embodiment, after the step S11, the electrode layer 530 is further deposited (step S12) on the vibrating film 412 using the same electrode material as that of the upper electrode 52 as shown in the second part of FIG. 13. As such, the electrode layer 530 is deposited with larger film thickness dimension than that of the upper electrode 52.

Subsequently, patterning using etching is performed on the electrode layer 530 to form (step S13) the connection electrode 53 as shown in the third part of FIG. 13. By providing the connection electrode 53 to the void 512A, it becomes possible for the lower electrode main body 511 and the lower electrode connection part 512 to be electrically connected via the connection electrode 53.

Functions and Advantages of Present Embodiment

In the piezoelectric element 5 according to the present embodiment, the void 512A is formed on the lower electrode main body 511 side of the lower electrode connection part 512, and thus, a part of the lower electrode connection part 512 is separated from the lower electrode main body 511. Further, the connection electrode 53 independent of the upper electrode 52 is disposed separately from the upper electrode 52 (the upper electrode main body 521) constituting the active section 50 of the piezoelectric element 5, and the connection electrode 53 is continuously formed from the piezoelectric outer periphery 62 of the piezoelectric film 6 to the lower electrode connection part 512 to have contact with the lower electrode main body 511 and the lower electrode connection part 512.

Therefore, it results that the connection electrode 53 electrically connects the lower electrode main body 511 and the lower electrode connection part 512 to each other, and thus, it is possible to prevent the problem that breaking occurs between the lower electrode main body 511 and the lower electrode connection part 512. Therefore, it is possible to appropriately input a drive signal to the lower electrode main body 511 constituting the active section 50 from the lower electrode connection part 512, and thus, the reliability of the piezoelectric element 5 can be enhanced.

Further, since the connection electrode 53 is disposed in the void between the lower electrode main body 511 and the lower electrode connection part 512, breaking between the lower electrode main body 511 and the lower electrode connection part 512 can be prevented, and thus, the reliability of the piezoelectric element can be made higher.

Further, in the present embodiment, the connection electrode 53 is formed to be larger in thickness dimension than the upper electrode 52. Therefore, the electrical resistance of the lower electrode connection part 512 covered with the connection electrode 53 is reduced, and thus, it is possible to suppress the influence such as the voltage drop in the drive signal input to the lower electrode main body 511 from the lower electrode connection part 512. Further, since the thickness dimension of the upper electrode 52 can be decreased, the thickness dimension of the active section 50 can also be decreased accordingly to thereby increase the displacement of the active section 50. Therefore, the transmission/reception sensitivity to the ultrasonic wave in the ultrasonic transducer Tr can be improved.

Third Embodiment

Next, a third embodiment of the invention will be described.

In the first embodiment described above, there is illustrated the configuration of the ultrasonic probe 2 having the ultrasonic device 22 equipped with the piezoelectric element 5 housed in the housing 21, and the ultrasonic measurement apparatus 1 equipped with the ultrasonic probe 2 to perform ultrasonic measurement. In contrast, it is also possible for the piezoelectric element 5 and the piezoelectric actuator equipped with the piezoelectric element 5 to be applied to other electronic apparatuses, and in the third embodiment, there will be described a liquid jet apparatus as an example of such other electronic apparatuses.

Figure 14:
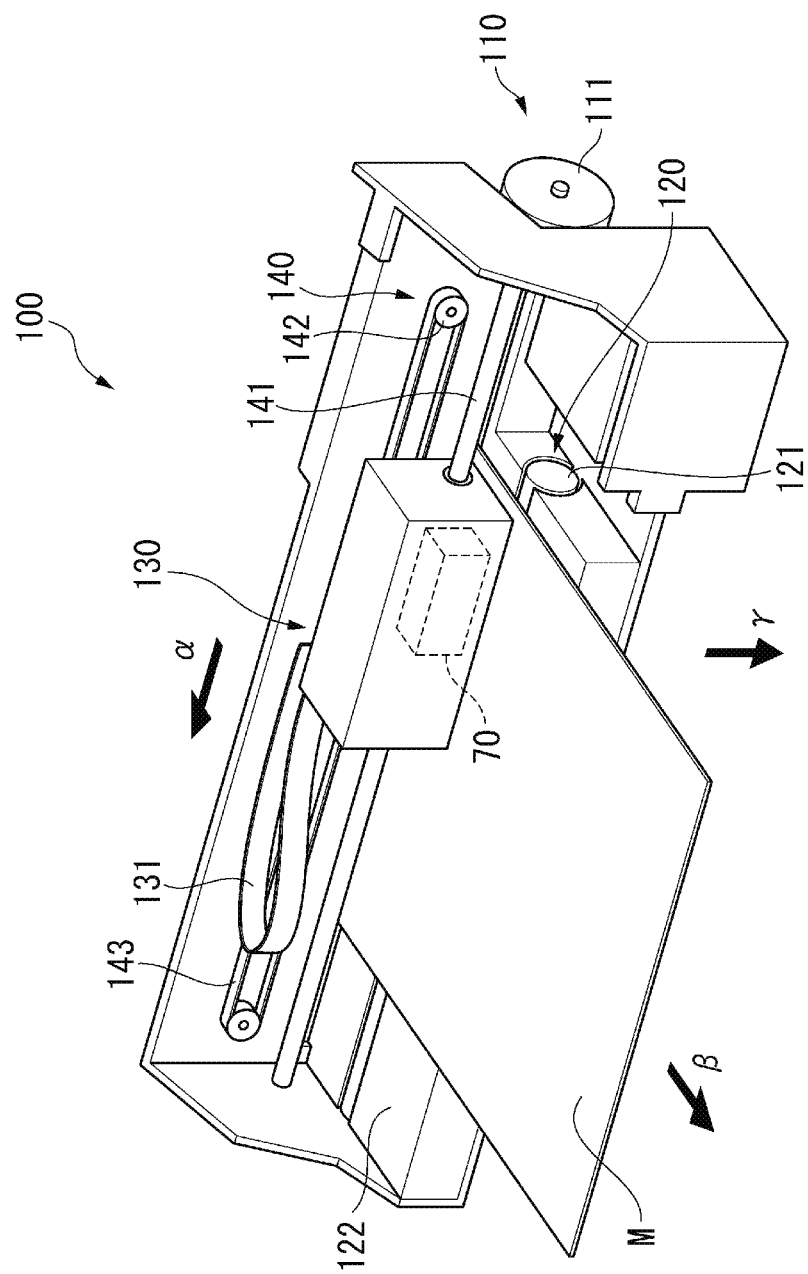
FIG. 14 is a diagram showing a configuration example of an appearance of a printer according to a third embodiment of the invention.
Figure 15:
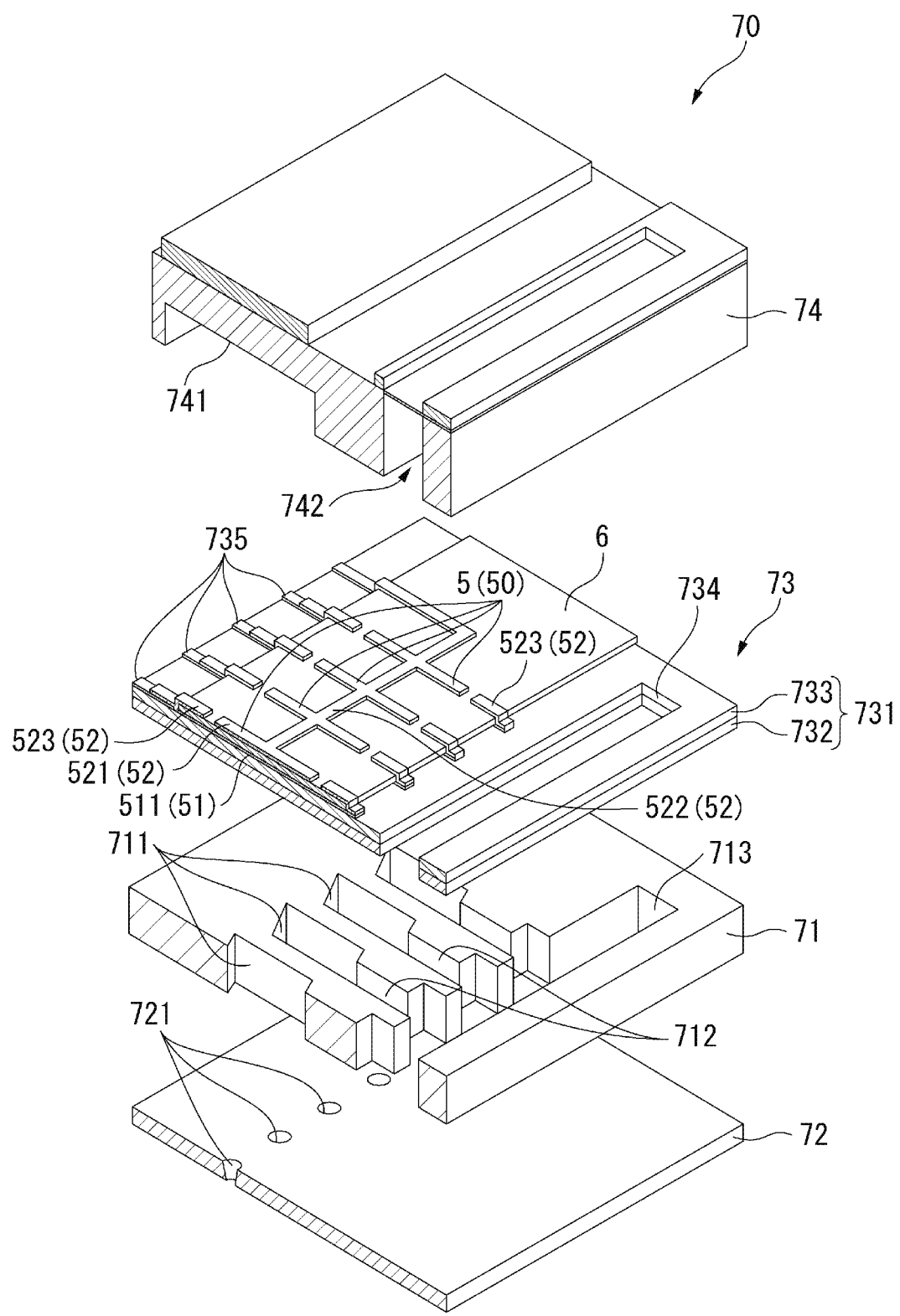
FIG. 15 is an exploded perspective view of a recording head provided to the printer according to the third embodiment.

FIG. 14 is a diagram showing a configuration example of an appearance of a printer 100 as an application example of a recording apparatus equipped with the piezoelectric element according to the invention. FIG. 15 is an exploded perspective view schematically showing the recording head 70 provided to the printer 100.

The printer 100 corresponds to the liquid jet apparatus, and is provided with a supply unit 110 for supplying a medium, a conveying unit 120 for conveying the medium, a carriage 130 attached with a recording head 70, a carriage moving unit 140 for moving the carriage 130, a control unit (not shown) for controlling the printer 100 as shown in FIG. 14. The printer 100 controls the units 110, 120, and 140 and the carriage 130 based on print data input from external equipment such as a personal computer to print an image on the medium M.

The supply unit 110 supplies the medium M at an image formation position. For example, the supply unit 110 is provided with a roll body 111 around which the medium M is wound, a roll driving motor (not shown), and a roll driving gear train (not shown). Further, based on a command from the control unit, the roll driving motor is rotationally driven, and the rotational force of the roll driving motor is transmitted to the roll body 111 via the roll driving gear train. Thus, the roll body 111 rotates, and a paper sheet wound around the roll body 111 is supplied on the downstream side (+β side) in the β direction (a sub-scanning direction).

The conveying unit 120 conveys the medium M supplied from the supply unit 110 along the β direction. For example, the conveying unit 120 is provided with a conveying roller 121, a driven roller (not shown) disposed across the medium M from the conveying roller 121 to be driven by the conveying roller 121, and a platen 122 disposed on the downstream side in the β direction of the conveying roller 121. The driving force from the roll driving motor not shown is transmitted to the conveying roller 121, and when the roll driving motor is driven by the control of the control unit (not shown), the conveying roller 121 is rotationally driven by the rotational force, and the conveying roller 121 conveys the medium M along the β direction in the state of sandwiching the medium M between the driven roller and the conveying roller 121.

The carriage 130 carries the recording head 70 for printing the image on the medium M. The recording head 70 is connected to the control unit via a cable 131. The recording head 70 will be described later. The carriage 130 is disposed so as to be movable along an α direction (a main scanning direction) crossing the β direction due to the carriage moving unit 140.

The carriage moving unit 140 reciprocates the carriage 130 along the α direction. For example, the carriage moving unit 140 is provided with a carriage guide shaft 141, a carriage motor 142, and a timing belt 143. The carriage guide shaft 141 is disposed along the α direction, and both end parts of the carriage guide shaft 141 are fixed to the housing of the printer 100. The carriage motor 142 drives the timing belt 143. The timing belt 143 is supported roughly in parallel to the carriage guide shaft 141, and a part of the carriage 130 is fixed to the timing belt 143. When the carriage motor 142 is driven based on the command of the control unit, the timing belt 143 is made to run forward and backward, and the carriage 130 fixed to the timing belt 143 reciprocates while being guided by the carriage guide shaft 141.

The recording head 70 corresponds to the liquid jet head, and ejects ink supplied from an ink tank (not shown) toward a γ direction crossing the α direction and the β direction to form the image on the medium M. As shown in FIG. 15, the recording head 70 is provided with a pressure chamber forming substrate 71, a nozzle plate 72, an actuator unit 73, and a sealing plate 74.

The pressure chamber forming substrate 71 is a plate member formed of, for example, a silicon single-crystal substrate. The pressure chamber forming substrate 71 is provided with a plurality of pressure chambers 711, ink supply channels 711 for supplying these pressure chambers 712 with the ink, and a communication part 712 communicated with each of the pressure chambers 711 via the respective ink supply channels 713.

The plurality of pressure chambers 711 is disposed so as to correspond one-to-one to the nozzles 721 constituting a nozzle row provided to the nozzle plate 72 as described later. Specifically, the pressure chambers 711 are formed along the nozzle row direction at the same pitch as the formation pitch of the nozzles 721.

The communication part 713 is formed along the plurality of pressure chambers 711. The communication part 713 is communicated with a communication aperture part 731 of the vibrating plate 734 described later and a liquid chamber space part 742 of the sealing plate 74, and is filled with the ink supplied from the ink tank (not shown). The ink with which the communication part 713 is filled is supplied to the pressure chambers 712 via the ink supply channels 711. In other words, the communication part 713 constitutes a reservoir (a common liquid chamber) as an ink chamber common to the pressure chambers 711.

It should be noted that the ink supply channels 712 are each a part formed to have the width narrower than that of the pressure chamber 711 to function as a flow pass resistance with respect to the ink flowing from the communication part 713 into the pressure chamber 711.

The nozzle plate 72 is provided with the nozzle row constituted by the plurality of nozzles 721, and is bonded to one surface (a surface on the opposite side to the actuator unit 73) of the pressure chamber forming substrate 71. The plurality of nozzles 721 is formed at the pitch corresponding to the dot formation density (e.g., 300 dpi). It should be noted that the nozzle plate 72 is formed of, for example, glass ceramics, a silicon single-crystal substrate, or stainless steel.

The actuator unit 73 is configured including the vibrating plate 731 (the driver) disposed on the opposite side to the nozzle plate 72 of the pressure chamber forming substrate 71, and the piezoelectric elements 5 stacked on the vibrating plate 731.

The vibrating plate 731 includes an elastic film 732 formed on the pressure chamber forming substrate 71, and an insulator film 732 formed on the elastic film 733. It should be noted that as the elastic film 732, there is preferably used, for example, silicon dioxide ($SiO_2$) having the thickness of 300 through 2000 nm. Further, as the insulator film 733, there is preferably used, for example, zirconium oxide ($ZrO_x$) having the thickness of 30 through 600 nm. The area for blocking the pressure camber 711 of the vibrating plate 731 is an area (a flexible part) allowed to make a distortional deformation in the direction of coming closer to and getting away from the nozzle 721 due to the drive of the piezoelectric element 5. It should be noted that the part corresponding to the communication part 713 of the pressure chamber forming substrate 71 in the vibrating plate 731 is provided with a communication aperture part 734 communicated with the communication part 713.

The piezoelectric elements 5 each have substantially the same configuration as that in the first embodiment or the second embodiment described above. The piezoelectric element 5 is disposed at the position corresponding to the pressure chamber 711 to constitute the piezoelectric actuator together with the flexible part as the area blocking the pressure chamber 711 of the vibrating plate 731. It should be noted that although not shown in the drawings, the lower electrode 51 and the upper electrode 52 are connected to the electrode terminals formed in the terminal area using leading electrodes 735.

It should be noted that although in FIG. 15, there is illustrated the configuration in which a groove part connecting non-coated parts of the plurality of piezoelectric elements 5 disposed along one direction is formed, this is not a limitation, and it is also possible to provide groove parts individually to the piezoelectric elements 5.

The sealing plate 74 is bonded to the surface on the opposite side to the pressure chamber forming substrate 71 of the actuator unit 73. On the surface located on the actuator unit 73 side of the sealing plate 74, there is formed a housing space part 741 capable of housing the piezoelectric elements 5. Further, in an area corresponding to the communication aperture 734 and the communication part 713 of the sealing plate 74, there is disposed the liquid chamber space part 742. The liquid chamber space part 742 is communicated with the communication aperture 734 and the communication part 713 to constitute the reservoir functioning as the ink chamber common to the pressure chambers 711. It should be noted that although not shown in the drawings, the sealing plate 74 is provided with a wiring aperture penetrating in the thickness direction at a position corresponding to the terminal areas of the actuator unit 73. In the wiring aperture, there are exposed the electrode terminals in the terminal areas described above. These electrode terminals are connected to wiring members not shown connected to the printer main body.

In the recording head 70 having such a configuration, the ink is introduced from an ink cartridge to fill the reservoir, the ink supply channels 712, the pressure chambers 711, and the flow channels to the nozzles 721 with the ink. Then, when the piezoelectric elements 5 corresponding respectively to the pressure chambers 711 are driven due to the supply of the drive signal from the printer main body, the areas (the flexible parts) corresponding to the pressure chambers 711 of the vibrating plate 731 are displaced to cause pressure variations in the respective pressure chambers 711. By controlling the pressure variations, the ink is ejected from the respective nozzles 721.

In a printer 100 such as described above, since the piezoelectric elements 5 described in the above embodiments are provided to the recording head 70, the equipment reliability of the recording head 70 can be enhanced, and at the same time, the equipment reliability of the printer 100 can also be enhanced.

Modified Examples

It should be noted that the invention is not limited to each of the embodiments described above, but includes modifications and improvements within a range where the advantages of the invention can be achieved, and configurations, which can be obtained by, for example, arbitrarily combining the embodiments.

In the second embodiment described above, there is shown the example in which the lower electrode main body 511 as the first electrode layer and the lower electrode connection part 512 as the first conductive layer are formed at the same time in the step S1, but this is not a limitation.

For example, the electrode material is deposited on the vibrating film 412, and then the lower electrode main body 511 as the first electrode layer is formed by etching. Subsequently, the electrode material is deposited once again, and then the lower electrode connection part 512 as the first conductive layer is patterned by etching. In such a configuration, it is also possible to form the lower electrode main body 511 and the lower electrode connection part 512 to have respective thickness dimensions different from each other. For example, it is possible to make the thickness dimension of the lower electrode main body 511 driven as the active section 50 smaller compared to that of the lower electrode connection part 512, and it is possible to make the thickness dimension of the lower electrode connection part 512 larger in order to reduce the electrical resistance.

In the second embodiment, the upper electrode 52 is formed in the step S4 and the step S11, and then the connection electrode 53 is formed in the step S12 and the step S13. In contrast, it is also possible to perform, for example, the step S12 and the step S13 in advance to form the connection electrode 53, and then perform the step S4 and the step S11 to form the upper electrode 52.

In each of the embodiments described above, there is shown the example in which the void (the void 512A) between the lower electrode main body 511 and the lower electrode connection part 512 is filled with the connection electrode part 523 (or the connection electrode 53) to thereby electrically connect the lower electrode main body 511 and the lower electrode connection part 512 to each other, but this example is not a limitation.

For example, it is also possible to adopt a configuration in which the connection electrode part 523 (or the connection electrode 53) is provided with a first extending part extending toward the +X side so as to overlap a part of the lower electrode main body 511 in the X-Y plane, a second extending part extending toward the +X side so as to overlap a part of the lower electrode connection part 512, and a connection part for connecting the first extending part and the second extending part to each other.

Further, there is shown the example in which the connection electrode part 523 (or the connection electrode 53) is continuously disposed from the piezoelectric outer periphery 62 in the upper surface (the surface on the opposite side to the element substrate 41) of the piezoelectric film 6 to the lower electrode connection part 512, but this is not a limitation. For example, it is also possible for the connection electrode part 523 (or the connection electrode 53) to be continuously disposed from a tilted surface tilted from the upper surface to the lower surface (the surface on the element substrate 41 side) in the outer edge part of the piezoelectric film 6 to the lower electrode connection part 512. Further, it is also possible to adopt a configuration in which the connection electrode part 523 (or the connection electrode 53) does not overlap the piezoelectric film 6 but is disposed on the void 512A in a pinpoint manner to have contact with the lower electrode main body 511 and the lower electrode connection part 512.

Although in each of the embodiments, the lower electrode 51, the upper electrode 52, and the connection electrode 53 are formed of a metal material, this is not a limitation. For example, it is also possible for the upper electrode 52 and the connection electrode 53 to be formed using a tin oxide type conductive material such as indium tin oxide (ITO) or fluorine-doped tin oxide (FTO), a zinc oxide type conductive material, an oxide conductive material such as strontium ruthenate ($SrRuO_3$), lanthanum nickelate ($LaNiO_3$), or element-doped strontium titanate, or a conductive polymer.

Although in each of the embodiments, the active section 50 of the piezoelectric element 5 is formed inside the outer peripheral edge of the aperture 411A (the flexible membrane 412A) in the plan view, this is not a limitation. For example, it is also possible for the outer peripheral edge of the active section 50 to be located outside the outer peripheral edge of the aperture 411A (the flexible membrane 412A).

In each of the embodiments described above, there is illustrated the configuration in which the piezoelectric element 5 and the sealing plate 42 are disposed on the opposite side to the substrate main body 411 (the aperture 411A) of the vibrating film 412, the acoustic layer 43 and the acoustic lens 44 are provided to the substrate main body 411, and the transmission and the reception of the ultrasonic wave are performed through the surface on the substrate main body 411 side, but this is not a limitation. For example, the piezoelectric element 5, the acoustic layer 43 and the acoustic lens 44 are provided on the opposite side to the substrate main body 411 of the vibrating film 412, the sealing plate 42 (a reinforcing plate) is provided on the substrate main body 411 side, and the transmission and the reception of the ultrasonic wave are performed through the surface on the opposite side to the substrate main body 411.

In each of the embodiments described above, the ultrasonic measurement apparatus 1 taking an organ in a living body as the measurement object, and the printer 100 are illustrated as the electronic apparatuses, but this is not a limitation. For example, the configurations of the embodiments and the modified examples described above can be applied to a measurement apparatus taking a variety of types of structures as the measurement object, and performing the detection of the defects and inspection of aging of the structures. Further, the same applies to a measurement apparatus taking, for example, a semiconductor package or a wafer as the measurement object, and detecting the defects of the measurement object.

Besides the above, specific structures to be adopted when implementing the invention can be configured by arbitrarily combining the embodiments and the modified examples described above with each other, or can arbitrarily be replaced with other structures within the range in which the advantages of the invention can be achieved.

The entire disclosure of Japanese Patent Application no. 2017-061459 filed Mar. 27, 2017 is expressly incorporated herein by reference.

What is claimed is:

1. A piezoelectric element comprising:
    a first electrode layer;
    a piezoelectric layer stacked on the first electrode layer; and
    a second electrode layer stacked on the piezoelectric layer,
    wherein the first electrode layer has a first part overlapping the piezoelectric layer in a plan view, and a second part at least partially separated from the first part and not overlapping the piezoelectric layer in the plan view,
    the second electrode layer has a third part overlapping the piezoelectric layer in the plan view, and a fourth part separated from the third part, and
    the fourth part is in contact with the first part and the second part.

2. The piezoelectric element according to claim 1, wherein
    the fourth part is disposed in a void between the first part and the second part.

3. A piezoelectric element comprising:
    a first electrode layer;

a piezoelectric layer stacked on the first electrode layer;

a second electrode layer stacked on the piezoelectric layer; and a first conductive layer and a second conductive layer both overlapping the piezoelectric layer in a plan view, wherein the first conductive layer is partially separated from the first electrode layer, and does not overlap the piezoelectric layer in the plan view, the second conductive layer is separated from the second electrode layer, and the second conductive layer is in contact with the first electrode layer and the first conductive layer.

4. The piezoelectric element according to claim 3, wherein the second conductive layer is thicker than the second electrode layer.

5. The piezoelectric element according to claim 3, wherein the second conductive layer is disposed in a void between the first electrode layer and the first conductive layer.

6. A piezoelectric actuator comprising:
the piezoelectric element according to claim 1; and
a driver driven by the piezoelectric element.

7. A piezoelectric actuator comprising:
the piezoelectric element according to claim 2; and
a driver driven by the piezoelectric element.

8. A piezoelectric actuator comprising:
the piezoelectric element according to claim 3; and
a driver driven by the piezoelectric element.

9. A piezoelectric actuator comprising:
the piezoelectric element according to claim 4; and
a driver driven by the piezoelectric element.

10. A piezoelectric actuator comprising:
the piezoelectric element according to claim 5; and
a driver driven by the piezoelectric element.

11. An ultrasonic apparatus comprising:
the piezoelectric actuator according to claim 6; and
a controller configured to control the piezoelectric actuator,
wherein the piezoelectric element drives the driver to one of transmit and receive an ultrasonic wave.

12. An electronic apparatus comprising:
the piezoelectric element according to claim 1; and
a controller configured to control the piezoelectric element.

13. An electronic apparatus comprising:
the piezoelectric element according to claim 2; and
a controller configured to control the piezoelectric element.

14. An electronic apparatus comprising:
the piezoelectric element according to claim 3; and
a controller configured to control the piezoelectric element.

15. An electronic apparatus comprising:
the piezoelectric element according to claim 4; and
a controller configured to control the piezoelectric element.

16. An electronic apparatus comprising:
the piezoelectric element according to claim 5; and
a controller configured to control the piezoelectric element.

* * * * *